US012708747B2

(12) United States Patent
Howell et al.

(10) Patent No.: US 12,708,747 B2
(45) Date of Patent: Aug. 18, 2026

(54) RAPIDLY INSERTABLE CENTRAL CATHETER INSERTION ASSEMBLIES AND METHODS

(71) Applicant: Bard Access Systems, Inc., Salt Lake City, UT (US)

(72) Inventors: Glade H. Howell, Draper, UT (US); Daniel B. Blanchard, Bountiful, UT (US); Eric W. Lindekugel, Salt Lake City, UT (US); Kyle G. Thornley, Farmington, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 950 days.

(21) Appl. No.: 17/882,388

(22) Filed: Aug. 5, 2022

(65) Prior Publication Data

US 2023/0042898 A1 Feb. 9, 2023

Related U.S. Application Data

(60) Provisional application No. 63/229,862, filed on Aug. 5, 2021.

(51) Int. Cl.
*A61M 25/06* (2006.01)
*A61M 25/00* (2006.01)
*A61M 25/01* (2006.01)

(52) U.S. Cl.
CPC .... *A61M 25/0606* (2013.01); *A61M 25/0097* (2013.01); *A61M 2025/0183* (2013.01); *A61M 25/06* (2013.01); *A61M 25/0668* (2013.01)

(58) Field of Classification Search
CPC ...... A61M 25/0668; A61M 2025/0183; A61M 25/09041; A61M 25/0097
(Continued)

(56) References Cited

U.S. PATENT DOCUMENTS

| | | | |
|---|---|---|---|
| 1,013,691 | A | 1/1912 | Shields |
| 3,225,762 | A | 12/1965 | Guttman |

(Continued)

FOREIGN PATENT DOCUMENTS

| | | | |
|---|---|---|---|
| DE | 202012006191 | U1 | 7/2012 |
| EP | 0653220 | A1 | 5/1995 |

(Continued)

OTHER PUBLICATIONS

U.S. Appl. No. 17/234,611, filed Apr. 19, 2021 Final Office Action dated Sep. 20, 2024.

(Continued)

*Primary Examiner* — Emily L Schmidt
*Assistant Examiner* — Martin A Radomski
(74) *Attorney, Agent, or Firm* — Rutan & Tucker LLP

(57) ABSTRACT

Disclosed are rapidly insertable central catheter ("RICC") insertion assemblies and methods. For example, a RICC insertion assembly can include a RICC, an access guidewire, an introducer needle, and a coupler coupling the foregoing components together. The introducer needle can include a needle shaft and a sheath. The needle shaft can include a longitudinal needle slot. The sheath can seal the needle slot thereunder except for a sheath opening thereto in a proximal portion of the sheath. The coupler can include a coupler housing and a valve module disposed in the coupler housing. The valve module can seal the needle shaft and the sheath therein. The access guidewire can include a proximal end coupled to the coupler and a distal end disposed in the introducer needle, thereby enforcing a loop in the access guidewire. The RICC can be disposed over the loop in a ready-to-deploy state of the RICC insertion assembly.

14 Claims, 16 Drawing Sheets

(58) Field of Classification Search
USPC .................................................... 604/164.1
See application file for complete search history.

(56) References Cited

U.S. PATENT DOCUMENTS 3,325,061 A 6/1967 Ellsworth
3,382,872 A 5/1968 Rubin
3,570,485 A 3/1971 Reilly
3,890,976 A 6/1975 Bazell et al.
3,991,762 A 11/1976 Radford
4,205,675 A 6/1980 Vaillancourt
4,292,970 A 10/1981 Hession, Jr.
4,445,893 A 5/1984 Bodicky
4,468,224 A 8/1984 Enzmann et al.
4,484,915 A 11/1984 Tartaglia
4,525,157 A 6/1985 Vaillancourt
4,581,019 A 4/1986 Curelaru et al.
4,582,181 A 4/1986 Samson
4,594,073 A 6/1986 Stine
4,639,248 A 1/1987 Schweblin
4,702,735 A 10/1987 Luther et al.
4,743,265 A 5/1988 Whitehouse et al.
4,766,908 A 8/1988 Clement
4,863,432 A 9/1989 Kvalo
4,935,008 A 6/1990 Lewis, Jr.
4,950,252 A 8/1990 Luther et al.
4,957,489 A 9/1990 Cameron et al.
4,994,040 A 2/1991 Cameron et al.
5,017,259 A 5/1991 Kohsai
5,040,548 A 8/1991 Yock
5,057,073 A 10/1991 Martin
5,112,312 A 5/1992 Luther
5,115,816 A 5/1992 Lee
5,120,317 A 6/1992 Luther
5,158,544 A 10/1992 Weinstein
5,167,634 A 12/1992 Corrigan, Jr. et al.
5,188,593 A 2/1993 Martin
5,195,962 A 3/1993 Martin et al.
5,207,650 A 5/1993 Martin
RE34,416 E 10/1993 Lemieux
5,267,958 A 12/1993 Buchbinder et al.
5,290,241 A 3/1994 Kraus et al.
5,292,309 A 3/1994 Van Tassel et al.
5,295,970 A 3/1994 Clinton et al.
5,306,247 A 4/1994 Pfenninger
5,312,361 A 5/1994 Zadini et al.
5,322,512 A 6/1994 Mohiuddin
5,328,472 A 7/1994 Steinke et al.
5,350,358 A 9/1994 Martin
5,358,495 A 10/1994 Lynn
5,364,355 A 11/1994 Alden et al.
5,368,567 A 11/1994 Lee
5,378,230 A 1/1995 Mahurkar
5,380,290 A 1/1995 Makower et al.
5,389,087 A 2/1995 Miraki
5,439,449 A 8/1995 Mapes et al.
5,443,457 A 8/1995 Ginn et al.
5,460,185 A 10/1995 Johnson et al.
5,489,271 A 2/1996 Andersen
5,573,520 A 11/1996 Schwartz et al.
5,584,813 A 12/1996 Livingston et al.
5,662,622 A 9/1997 Gore et al.
5,683,370 A 11/1997 Luther et al.
5,713,876 A 2/1998 Bogert et al.
5,718,678 A 2/1998 Fleming, III
5,772,636 A 6/1998 Brimhall et al.
5,885,251 A 3/1999 Luther
5,919,164 A 7/1999 Andersen
5,921,971 A 7/1999 Agro et al.
5,947,940 A 9/1999 Beisel
5,951,518 A 9/1999 Licata et al.
5,957,893 A 9/1999 Luther et al.
5,971,957 A 10/1999 Luther et al.
6,159,198 A 12/2000 Gardeski et al.
6,197,007 B1 3/2001 Thorne et al.
6,206,849 B1 3/2001 Martin et al.
6,228,062 B1 5/2001 Howell et al.
6,273,874 B1 8/2001 Parris
6,475,187 B1 11/2002 Gerberding
6,533,782 B2 3/2003 Howell et al.
6,551,284 B1 4/2003 Greenberg et al.
6,606,515 B1 8/2003 Windheuser et al.
6,616,630 B1 9/2003 Woehr et al.
6,626,868 B1 9/2003 Prestidge et al.
6,626,869 B1 9/2003 Bint
6,638,252 B2 10/2003 Moulton et al.
6,716,228 B2 4/2004 Tal
6,726,659 B1 4/2004 Stocking et al.
6,819,951 B2 11/2004 Patel et al.
6,821,287 B1 11/2004 Jang
6,926,692 B2 8/2005 Katoh et al.
6,962,575 B2 11/2005 Tal
6,991,625 B1 1/2006 Gately et al.
6,994,693 B2 2/2006 Tal
6,999,809 B2 2/2006 Currier et al.
7,025,746 B2 4/2006 Tal
7,029,467 B2 4/2006 Currier et al.
7,037,293 B2 5/2006 Carrillo et al.
7,074,231 B2 7/2006 Jang
7,094,222 B1 8/2006 Siekas et al.
7,141,050 B2 11/2006 Deal et al.
7,144,386 B2 12/2006 Korkor et al.
7,311,697 B2 12/2007 Osborne
7,364,566 B2 4/2008 Elkins et al.
7,377,910 B2 5/2008 Katoh et al.
7,390,323 B2 6/2008 Jang
D600,793 S 9/2009 Bierman et al.
D601,242 S 9/2009 Bierman et al.
D601,243 S 9/2009 Bierman et al.
7,594,911 B2 9/2009 Powers et al.
7,691,093 B2 4/2010 Brimhall
7,722,567 B2 5/2010 Tal
D617,893 S 6/2010 Bierman et al.
D624,643 S 9/2010 Bierman et al.
7,819,889 B2 10/2010 Healy et al.
7,857,788 B2 12/2010 Racz
D630,729 S 1/2011 Bierman et al.
7,909,797 B2 3/2011 Kennedy, II et al.
7,909,811 B2 3/2011 Agro et al.
7,922,696 B2 4/2011 Tal et al.
7,938,820 B2 5/2011 Webster et al.
7,967,834 B2 6/2011 Tal et al.
7,976,511 B2 7/2011 Fojtik
7,985,204 B2 7/2011 Katoh et al.
8,073,517 B1 12/2011 Burchman
8,105,286 B2 1/2012 Anderson et al.
8,192,402 B2 6/2012 Anderson et al.
8,202,251 B2 6/2012 Bierman et al.
8,206,356 B2 6/2012 Katoh et al.
8,361,011 B2 1/2013 Mendels
8,372,107 B2 2/2013 Tupper
8,377,006 B2 2/2013 Tal et al.
8,454,577 B2 6/2013 Joergensen et al.
8,585,858 B2 11/2013 Kronfeld et al.
8,657,790 B2 2/2014 Tal et al.
8,672,888 B2 3/2014 Tal
8,696,645 B2 4/2014 Tal et al.
8,784,362 B2 7/2014 Boutilette et al.
8,827,958 B2 9/2014 Bierman et al.
8,876,704 B2 11/2014 Golden et al.
8,882,713 B1 11/2014 Call et al.
8,900,192 B2 12/2014 Anderson et al.
8,900,207 B2 12/2014 Uretsky
8,915,884 B2 12/2014 Tal et al.
8,956,327 B2 2/2015 Bierman et al.
9,023,093 B2 5/2015 Pal
9,067,023 B2 6/2015 Bertocci
9,126,012 B2 9/2015 McKinnon et al.
9,138,252 B2 9/2015 Bierman et al.
9,180,275 B2 11/2015 Helm
9,265,920 B2 2/2016 Rundquist et al.
9,272,121 B2 3/2016 Piccagli
9,445,734 B2 9/2016 Grunwald
9,522,254 B2 12/2016 Belson

(56) References Cited

U.S. PATENT DOCUMENTS 9,554,785 B2 1/2017 Walters et al.
9,566,087 B2 2/2017 Bierman et al.
9,675,784 B2 6/2017 Belson
9,713,695 B2 7/2017 Bunch et al.
9,764,117 B2 9/2017 Bierman et al.
9,770,573 B2 9/2017 Golden et al.
9,814,861 B2 11/2017 Boutillette et al.
9,820,845 B2 11/2017 von Lehe et al.
9,861,383 B2 1/2018 Clark
9,872,971 B2 1/2018 Blanchard
9,884,169 B2 2/2018 Bierman et al.
9,889,275 B2 2/2018 Voss et al.
9,913,585 B2 3/2018 McCaffrey et al.
9,913,962 B2 3/2018 Tal et al.
9,981,113 B2 5/2018 Bierman
10,010,312 B2 7/2018 Tegels
10,065,020 B2 9/2018 Gaur
10,086,170 B2 10/2018 Chhikara et al.
10,098,724 B2 10/2018 Adams et al.
10,111,683 B2 10/2018 Tsamir et al.
10,118,020 B2 11/2018 Avneri et al.
10,130,269 B2 11/2018 McCaffrey et al.
10,220,184 B2 3/2019 Clark
10,220,191 B2 3/2019 Belson et al.
10,265,508 B2 4/2019 Baid
10,271,873 B2 4/2019 Steingisser et al.
10,376,675 B2 8/2019 Mitchell et al.
10,675,440 B2 6/2020 Abitabilo et al.
10,688,281 B2 6/2020 Blanchard et al.
10,806,901 B2 10/2020 Burkholz et al.
10,926,060 B2 2/2021 Stern et al.
11,260,206 B2 3/2022 Stone et al.
11,400,260 B2 8/2022 Huang et al.
11,759,607 B1 9/2023 Biancarelli
2002/0040231 A1 4/2002 Wysoki
2002/0045843 A1 4/2002 Barker et al.
2002/0123755 A1 9/2002 Lowe et al.
2002/0198492 A1 12/2002 Miller et al.
2003/0036712 A1 2/2003 Heh et al.
2003/0060863 A1 3/2003 Dobak
2003/0088212 A1 5/2003 Tal
2003/0100849 A1 5/2003 Jang
2003/0153874 A1 8/2003 Tal
2003/0158514 A1 8/2003 Tal
2004/0015138 A1 1/2004 Currier et al.
2004/0049157 A1 3/2004 Plishka et al.
2004/0064086 A1 4/2004 Gottlieb et al.
2004/0092879 A1 5/2004 Kraus et al.
2004/0116864 A1 6/2004 Boudreaux
2004/0116901 A1 6/2004 Appling
2004/0167478 A1 8/2004 Mooney et al.
2004/0193093 A1 9/2004 Desmond
2004/0230178 A1 11/2004 Wu
2005/0004554 A1 1/2005 Osborne
2005/0120523 A1 6/2005 Schweikert
2005/0131343 A1 6/2005 Abrams et al.
2005/0148936 A1* 7/2005 Moss ................. A61B 17/3403 604/116
2005/0215956 A1 9/2005 Nerney
2005/0215958 A1 9/2005 Hawthorne
2005/0245882 A1 11/2005 Elkins et al.
2005/0283221 A1 12/2005 Mann et al.
2006/0009740 A1 1/2006 Higgins et al.
2006/0116629 A1 6/2006 Tal et al.
2006/0129100 A1 6/2006 Tal
2006/0129130 A1 6/2006 Tal et al.
2006/0135973 A1 6/2006 Hawkins et al.
2007/0276288 A1 11/2007 Khaw
2008/0045894 A1 2/2008 Perchik et al.
2008/0091137 A1* 4/2008 Reavill ................. A61M 25/01 604/27
2008/0125744 A1 5/2008 Treacy
2008/0125748 A1 5/2008 Patel
2008/0132850 A1 6/2008 Fumiyama et al.
2008/0262430 A1 10/2008 Anderson et al.
2008/0262431 A1 10/2008 Anderson et al.
2008/0294111 A1 11/2008 Tal et al.
2008/0312578 A1 12/2008 DeFonzo et al.
2008/0319387 A1 12/2008 Amisar et al.
2009/0131872 A1 5/2009 Popov
2009/0187147 A1* 7/2009 Kurth ................... A61M 25/09 604/161
2009/0221961 A1 9/2009 Tal et al.
2009/0270889 A1 10/2009 Tal et al.
2009/0292272 A1 11/2009 McKinnon
2010/0030154 A1 2/2010 Duffy
2010/0256487 A1 10/2010 Hawkins et al.
2010/0298839 A1 11/2010 Castro
2010/0305474 A1 12/2010 DeMars et al.
2011/0004162 A1 1/2011 Tal
2011/0009827 A1* 1/2011 Bierman ............ A61B 17/3415 604/164.13
2011/0021994 A1 1/2011 Anderson et al.
2011/0066142 A1 3/2011 Tal et al.
2011/0071502 A1* 3/2011 Asai .................. A61M 25/0606 604/528
2011/0144620 A1 6/2011 Tal
2011/0152836 A1 6/2011 Riopelle et al.
2011/0190778 A1 8/2011 Arpasi et al.
2011/0202006 A1 8/2011 Bierman et al.
2011/0230844 A1 9/2011 Shaw et al.
2011/0251559 A1 10/2011 Tal et al.
2011/0270192 A1 11/2011 Anderson et al.
2012/0016346 A1 1/2012 Steinmetz et al.
2012/0041371 A1 2/2012 Tal et al.
2012/0065590 A1 3/2012 Bierman et al.
2012/0078231 A1 3/2012 Hoshinouchi
2012/0130411 A1 5/2012 Tal et al.
2012/0130415 A1 5/2012 Tal et al.
2012/0157854 A1 6/2012 Kurrus et al.
2012/0215171 A1 8/2012 Christiansen
2012/0220942 A1 8/2012 Hall et al.
2012/0226239 A1 9/2012 Green
2012/0283640 A1 11/2012 Anderson et al.
2012/0316500 A1 12/2012 Bierman et al.
2013/0046241 A1 2/2013 Okamura et al.
2013/0053763 A1 2/2013 Makino et al.
2013/0053826 A1 2/2013 Shevgoor
2013/0123704 A1 5/2013 Bierman et al.
2013/0158338 A1 6/2013 Kelly et al.
2013/0158506 A1 6/2013 Harris et al.
2013/0188291 A1 7/2013 Vardiman
2013/0237931 A1 9/2013 Tal et al.
2013/0306079 A1 11/2013 Tracy
2014/0025036 A1 1/2014 Bierman et al.
2014/0081210 A1 3/2014 Bierman et al.
2014/0094774 A1 4/2014 Blanchard
2014/0100552 A1 4/2014 Gallacher et al.
2014/0110296 A1 4/2014 Terzibashian
2014/0171833 A1 6/2014 Matsuno et al.
2014/0188211 A1 7/2014 Roeder et al.
2014/0207052 A1 7/2014 Tal et al.
2014/0207069 A1 7/2014 Bierman et al.
2014/0214005 A1 7/2014 Belson
2014/0221831 A1 8/2014 Kurrus et al.
2014/0257111 A1 9/2014 Yamashita et al.
2014/0276432 A1 9/2014 Bierman et al.
2014/0276599 A1 9/2014 Cully et al.
2014/0364766 A1 12/2014 Devgon et al.
2015/0011834 A1 1/2015 Ayala et al.
2015/0080939 A1 3/2015 Adams et al.
2015/0094653 A1 4/2015 Pacheco et al.
2015/0112307 A1 4/2015 Margolis
2015/0112310 A1 4/2015 Call et al.
2015/0119806 A1 4/2015 Blanchard et al.
2015/0126930 A1 5/2015 Bierman et al.
2015/0148595 A1 5/2015 Bagwell et al.
2015/0157829 A1 6/2015 Bunch et al.
2015/0190168 A1 7/2015 Bierman et al.
2015/0196210 A1 7/2015 McCaffrey et al.
2015/0224287 A1 8/2015 Bian et al.
2015/0231364 A1 8/2015 Blanchard et al.
2015/0283357 A1 10/2015 Lampropoulos et al.

(56) References Cited

U.S. PATENT DOCUMENTS

2015/0290431 A1* 10/2015 Hall .................... A61M 29/00 604/510
2015/0297868 A1 10/2015 Tal et al.
2015/0306356 A1 10/2015 Gill
2015/0320969 A1 11/2015 Haslinger et al.
2015/0320977 A1 11/2015 Vitullo et al.
2015/0351793 A1 12/2015 Bierman et al.
2015/0359549 A1 12/2015 Lenker et al.
2015/0359998 A1 12/2015 Carmel et al.
2016/0001046 A1* 1/2016 Tietze ............... A61M 25/0668 604/164.08
2016/0030716 A1* 2/2016 Mallin ............. A61M 25/0606 604/510
2016/0067391 A1 3/2016 Real et al.
2016/0082223 A1 3/2016 Barnell
2016/0114124 A1 4/2016 Tal
2016/0158523 A1 6/2016 Helm
2016/0220786 A1 8/2016 Mitchell et al.
2016/0220811 A1 8/2016 Spotnitz et al.
2016/0242661 A1 8/2016 Fischell et al.
2016/0256101 A1 9/2016 Aharoni et al.
2016/0256667 A1 9/2016 Ribelin et al.
2016/0325073 A1 11/2016 Davies et al.
2016/0331938 A1 11/2016 Blanchard et al.
2016/0338728 A1 11/2016 Tal
2016/0346503 A1 12/2016 Jackson et al.
2017/0028135 A1 2/2017 Fransson et al.
2017/0035990 A1 2/2017 Swift
2017/0072165 A1 3/2017 Lim et al.
2017/0120000 A1 5/2017 Osypka et al.
2017/0120014 A1 5/2017 Harding et al.
2017/0120034 A1 5/2017 Kaczorowski
2017/0128700 A1 5/2017 Roche Rebollo
2017/0156987 A1 6/2017 Babbs et al.
2017/0172653 A1 6/2017 Urbanski et al.
2017/0182293 A1 6/2017 Chhikara et al.
2017/0239443 A1 8/2017 Abitabilo et al.
2017/0259043 A1 9/2017 Chan et al.
2017/0273713 A1 9/2017 Shah et al.
2017/0274182 A1 9/2017 O'Bryan et al.
2017/0296792 A1 10/2017 Ornelas Vargas et al.
2017/0326339 A1 11/2017 Bailey et al.
2017/0361070 A1 12/2017 Hivert
2017/0368255 A1 12/2017 Provost et al.
2018/0001062 A1 1/2018 O'Carrol et al.
2018/0008294 A1 1/2018 Garrison et al.
2018/0021545 A1 1/2018 Mitchell et al.
2018/0116690 A1 5/2018 Sarabia et al.
2018/0117284 A1 5/2018 Appling et al.
2018/0133438 A1 5/2018 Hulvershorn et al.
2018/0154062 A1 6/2018 DeFonzo et al.
2018/0154112 A1 6/2018 Chan et al.
2018/0214674 A1 8/2018 Ebnet et al.
2018/0229004 A1 8/2018 Blanchard et al.
2018/0296799 A1 10/2018 Horst et al.
2018/0296804 A1 10/2018 Bierman
2018/0310955 A1 11/2018 Lindekugel et al.
2018/0369540 A1 12/2018 Asai
2019/0015646 A1 1/2019 Matlock et al.
2019/0021640 A1 1/2019 Burkholz et al.
2019/0038113 A1 2/2019 Chu
2019/0060616 A1 2/2019 Solomon
2019/0076167 A1 3/2019 Fantuzzi et al.
2019/0076628 A1 3/2019 Anstett
2019/0134349 A1 5/2019 Cohn et al.
2019/0192824 A1 6/2019 Cordeiro et al.
2019/0201665 A1 7/2019 Turpin
2019/0209812 A1 7/2019 Burkholz et al.
2019/0240459 A1 8/2019 Belson
2019/0255294 A1 8/2019 Mitchell et al.
2019/0255298 A1 8/2019 Mitchell et al.
2019/0275303 A1 9/2019 Tran et al.
2019/0276268 A1 9/2019 Akingba
2019/0282788 A1 9/2019 Stone et al.
2019/0321590 A1 10/2019 Burkholz et al.
2019/0351196 A1 11/2019 Ribelin et al.
2020/0001051 A1 1/2020 Huang et al.
2020/0016374 A1 1/2020 Burkholz et al.
2020/0046948 A1 2/2020 Burkholz et al.
2020/0100716 A1 4/2020 Devgon et al.
2020/0129732 A1 4/2020 Vogt et al.
2020/0147349 A1 5/2020 Holt
2020/0197579 A1 6/2020 Chu et al.
2020/0197682 A1 6/2020 Franklin et al.
2020/0197684 A1 6/2020 Wax
2020/0237278 A1 7/2020 Asbaghi
2020/0359995 A1 11/2020 Walsh et al.
2021/0030944 A1 2/2021 Cushen et al.
2021/0060306 A1 3/2021 Kumar
2021/0069471 A1 3/2021 Howell
2021/0085927 A1 3/2021 Howell
2021/0100985 A1 4/2021 Akcay et al.
2021/0113809 A1 4/2021 Howell
2021/0113810 A1 4/2021 Howell
2021/0113816 A1 4/2021 DiCianni
2021/0121661 A1 4/2021 Howell
2021/0121667 A1 4/2021 Howell
2021/0228842 A1 7/2021 Scherich et al.
2021/0228843 A1 7/2021 Howell et al.
2021/0244920 A1 8/2021 Kujawa et al.
2021/0290898 A1 9/2021 Burkholz
2021/0290901 A1 9/2021 Burkholz et al.
2021/0290913 A1 9/2021 Horst et al.
2021/0322729 A1 10/2021 Howell
2021/0330941 A1 10/2021 Howell et al.
2021/0330942 A1 10/2021 Howell
2021/0361915 A1 11/2021 Howell et al.
2021/0402149 A1 12/2021 Howell
2021/0402153 A1 12/2021 Howell et al.
2022/0001109 A1 1/2022 Simon
2022/0001138 A1 1/2022 Howell
2022/0032013 A1 2/2022 Howell et al.
2022/0032014 A1 2/2022 Howell et al.
2022/0062528 A1 3/2022 Thornley et al.
2022/0062596 A1 3/2022 Ribelin et al.
2022/0126064 A1 4/2022 Tobin et al.
2022/0193376 A1 6/2022 Spataro et al.
2022/0193377 A1 6/2022 Haymond et al.
2022/0193378 A1 6/2022 Spataro et al.
2022/0203075 A1 6/2022 Murphy
2022/0323723 A1 10/2022 Spataro et al.
2022/0331562 A1 10/2022 Jaros et al.
2022/0331563 A1 10/2022 Papadia
2023/0096377 A1 3/2023 West et al.
2023/0096740 A1 3/2023 Bechstein et al.
2023/0099654 A1 3/2023 Blanchard et al.
2023/0100482 A1 3/2023 Howell
2023/0101455 A1 3/2023 Howell et al.
2023/0102231 A1 3/2023 Bechstein et al.
2023/0173231 A1 6/2023 Parikh et al.
2023/0233814 A1 7/2023 Howell et al.
2023/0381459 A1 11/2023 Belson et al.
2023/0381481 A1 11/2023 Pizzato
2024/0009427 A1 1/2024 Howell et al.
2024/0050706 A1 2/2024 Howell et al.
2024/0198058 A1 6/2024 Howell et al.
2025/0001136 A1 1/2025 Mitchell et al.
2025/0065083 A1 2/2025 Haymond et al.
2025/0082906 A1 3/2025 Howell et al.
2025/0222237 A1 7/2025 Spataro et al.
2025/0235669 A1 7/2025 Howell

FOREIGN PATENT DOCUMENTS

EP 0730880 A1 9/1996
EP 2061385 A1 5/2009
EP 1458437 B1 3/2010
EP 2248549 A2 11/2010
EP 2319576 A1 5/2011
EP 2366422 A1 9/2011
EP 2486880 A2 8/2012
EP 2486881 A2 8/2012
EP 2486951 A2 8/2012
EP 2512576 A2 10/2012

(56) References Cited

FOREIGN PATENT DOCUMENTS

| | | | |
|---|---|---|---|
| EP | 2152348 | B1 | 2/2015 |
| EP | 3473291 | A1 | 4/2019 |
| EP | 3093038 | B1 | 5/2019 |
| EP | 2260897 | B1 | 9/2019 |
| EP | 3693051 | A1 | 8/2020 |
| GB | 1273547 | A | 5/1972 |
| JP | 2004248987 | A | 9/2004 |
| JP | 2008054859 | A | 3/2008 |
| WO | 94/21315 | A1 | 9/1994 |
| WO | 95/32009 | A2 | 11/1995 |
| WO | 98/44979 | A1 | 10/1998 |
| WO | 98/53871 | A1 | 12/1998 |
| WO | 9857685 | A1 | 12/1998 |
| WO | 99/12600 | A1 | 3/1999 |
| WO | 99/26681 | A1 | 6/1999 |
| WO | 00/06221 | A1 | 2/2000 |
| WO | 0054830 | A1 | 9/2000 |
| WO | 2003008020 | A1 | 1/2003 |
| WO | 2003057272 | A2 | 7/2003 |
| WO | 03/068073 | A1 | 8/2003 |
| WO | 2003066125 | A2 | 8/2003 |
| WO | 2005096778 | A2 | 10/2005 |
| WO | 2006055288 | A2 | 5/2006 |
| WO | 2006055780 | A2 | 5/2006 |
| WO | 2007046850 | A2 | 4/2007 |
| WO | 2008033983 | A1 | 3/2008 |
| WO | 2008092029 | A2 | 7/2008 |
| WO | 2008/131300 | A2 | 10/2008 |
| WO | 2008131289 | A2 | 10/2008 |
| WO | 2009114833 | A1 | 9/2009 |
| WO | 2009114837 | A2 | 9/2009 |
| WO | 2010/048449 | A2 | 4/2010 |
| WO | 2010056906 | A2 | 5/2010 |
| WO | 2010083467 | A2 | 7/2010 |
| WO | 2010/132608 | A2 | 11/2010 |
| WO | 2011081859 | A2 | 7/2011 |
| WO | 2011097639 | A2 | 8/2011 |
| WO | 2011109792 | A1 | 9/2011 |
| WO | 2011146764 | A1 | 11/2011 |
| WO | 2012068162 | A2 | 5/2012 |
| WO | 2012068166 | A2 | 5/2012 |
| WO | 2012135761 | A1 | 10/2012 |
| WO | 2012/154277 | A1 | 11/2012 |
| WO | 2012162677 | A1 | 11/2012 |
| WO | 2013026045 | A1 | 2/2013 |
| WO | 2013138519 | A1 | 9/2013 |
| WO | 2014006403 | A1 | 1/2014 |
| WO | 2014/100392 | A1 | 6/2014 |
| WO | 2014113257 | A2 | 7/2014 |
| WO | 2014152005 | A2 | 9/2014 |
| WO | 2014197614 | A2 | 12/2014 |
| WO | 2015057766 | A1 | 4/2015 |
| WO | 2015077560 | A1 | 5/2015 |
| WO | 2015/168655 | A2 | 11/2015 |
| WO | 2016110824 | A1 | 7/2016 |
| WO | 2016123278 | A1 | 8/2016 |
| WO | 2016139590 | A1 | 9/2016 |
| WO | 2016139597 | A2 | 9/2016 |
| WO | 2016/178974 | A1 | 11/2016 |
| WO | 2016/187063 | A1 | 11/2016 |
| WO | 2016176065 | A1 | 11/2016 |
| WO | 2018089275 | A1 | 5/2018 |
| WO | 2018089285 | A1 | 5/2018 |
| WO | 2018089385 | A1 | 5/2018 |
| WO | 2018191547 | A1 | 10/2018 |
| WO | 2018213148 | A1 | 11/2018 |
| WO | 2018218236 | A1 | 11/2018 |
| WO | 2019/050576 | A1 | 3/2019 |
| WO | 2019/146026 | A1 | 8/2019 |
| WO | 2019199734 | A1 | 10/2019 |
| WO | 2020014149 | A1 | 1/2020 |
| WO | 2020069395 | A1 | 4/2020 |
| WO | 2020/109448 | A1 | 6/2020 |
| WO | 2020/113123 | A1 | 6/2020 |
| WO | 2021038041 | A1 | 3/2021 |
| WO | 2021050302 | A1 | 3/2021 |
| WO | 2021/077103 | A1 | 4/2021 |
| WO | 2021062023 | A1 | 4/2021 |
| WO | 2021081205 | A1 | 4/2021 |
| WO | 2021086793 | A1 | 5/2021 |
| WO | 2021/236950 | A1 | 11/2021 |
| WO | 2021226050 | A1 | 11/2021 |
| WO | 2022/031618 | A1 | 2/2022 |
| WO | 2022/094141 | A1 | 5/2022 |
| WO | 2022/133297 | A1 | 6/2022 |
| WO | 2022-140406 | A1 | 6/2022 |
| WO | 2022/140429 | A1 | 6/2022 |
| WO | 2022/217098 | A1 | 10/2022 |
| WO | 2023014994 | A1 | 2/2023 |
| WO | 2023/049498 | A1 | 3/2023 |
| WO | 2023049505 | A1 | 3/2023 |
| WO | 2023049511 | A1 | 3/2023 |
| WO | 2023049519 | A1 | 3/2023 |
| WO | 2023049522 | A1 | 3/2023 |
| WO | 2023146792 | A1 | 8/2023 |

OTHER PUBLICATIONS

U.S. Appl. No. 17/240,591, filed Apr. 26, 2021 Final Office Action dated Aug. 14, 2024.

U.S. Appl. No. 17/557,924, filed Dec. 21, 2021 Non-Final Office Action dated Aug. 20, 2024.

U.S. Appl. No. 17/558,124, filed Dec. 21, 2021 Non-Final Office Action dated Sep. 20, 2024.

PCT/US2021/064671 filed Dec. 21, 2021 International Search Report and Written Opinion dated May 27, 2022.

PCT/US2022/024085 filed Apr. 8, 2022 International Search Report and Wirtten Opinion dated Sep. 12, 2022.

U.S. Appl. No. 16/398,020, filed Apr. 29, 2019 Examiner's Answer dated Oct. 31, 2022.

U.S. Appl. No. 17/031,478, filed Sep. 24, 2020 Notice of Allowance dated Sep. 16, 2022.

U.S. Appl. No. 17/156,252, filed Jan. 22, 2021 Non-Final Office Action dated Oct. 25, 2022.

U.S. Appl. No. 17/234,611, filed Apr. 19, 2021 Examiner's Answer dated May 1, 2025.

U.S. Appl. No. 17/390,682, filed Jul. 30, 2021 Final Office Action dated Feb. 28, 2025.

U.S. Appl. No. 17/392,061, filed Aug. 2, 2021 Advisory Action dated Mar. 12, 2025.

U.S. Appl. No. 17/392,061, filed Aug. 2, 2021 Non-Final Office Action dated Apr. 5, 2025.

U.S. Appl. No. 17/558,124, filed Dec. 21, 2021 Notice of Allowance dated Mar. 7, 2025.

U.S. Appl. No. 16/398,020, filed Apr. 29, 2019 Board Decision dated Oct. 30, 2023.

U.S. Appl. No. 17/237,909, filed Apr. 22, 2021 Notice of Allowance dated Oct. 27, 2023.

U.S. Appl. No. 17/240,591, filed Apr. 26, 2021 Final Office Action dated Dec. 6, 2023.

U.S. Appl. No. 17/358,504, filed Jun. 25, 2021 Non-Final Office Action dated Oct. 4, 2023.

U.S. Appl. No. 17/360,694, filed Jun. 28, 2021 Non-Final Office Action dated Oct. 13, 2023.

U.S. Appl. No. 17/390,682, filed Jul. 30, 2021 Non-Final Office Action dated Dec. 1, 2023.

U.S. Appl. No. 17/392,061, filed Aug. 2, 2021 Final Office Action dated Nov. 21, 2023.

U.S. Appl. No. 17/513,789, filed Oct. 28, 2021 Restriction Requirement dated Oct. 3, 2023.

U.S. Appl. No. 17/557,924, filed Dec. 21, 2021 Non-Final Office Action dated Nov. 3, 2023.

U.S. Appl. No. 17/360,694, filed Jun. 28, 2021 Notice of Allowance dated Dec. 16, 2024.

U.S. Appl. No. 17/392,061, filed Aug. 2, 2021 Final Office Action dated Jan. 2, 2025.

U.S. Appl. No. 17/461,619, filed Aug. 30, 2021 Non-Final Office Action dated Feb. 11, 2025.

(56) References Cited

OTHER PUBLICATIONS

U.S. Appl. No. 17/461,619, filed Aug. 30, 2021 Restriction Requirement dated Dec. 6, 2024.
U.S. Appl. No. 17/513,789, filed Oct. 28, 2021 Notice of Allowance dated Jan. 3, 2025.
U.S. Appl. No. 17/557,924, filed Dec. 21, 2021 Notice of Allowance dated Dec. 11, 2024.
U.S. Appl. No. 16/398,020, filed Apr. 29, 2019 Non-Final Office Action dated Jan. 18, 2024.
U.S. Appl. No. 17/234,611, filed Apr. 19, 2021 Restriction Requirement dated Jan. 18, 2024.
U.S. Appl. No. 17/240,591, filed Apr. 26, 2021 Advisory Action dated Feb. 22, 2024.
U.S. Appl. No. 17/360,694, filed Jun. 28, 2021 Non-Final Office Action dated Feb. 14, 2024.
U.S. Appl. No. 17/392,061, filed Aug. 2, 2021 Advisory Action dated Feb. 14, 2024.
U.S. Appl. No. 17/513,789, filed Oct. 28, 2021 Non-Final Office Action dated Jan. 9, 2024.
U.S. Appl. No. 17/557,924, filed Dec. 21, 2021 Final Office Action dated Feb. 29, 2024.
PCT/US2023/011173 filed Jan. 19, 2023 International Search Report and Written Opinion dated May 22, 2023.
U.S. Appl. No. 17/156,252, filed Jan. 22, 2021 Notice of Allowance dated Aug. 9, 2023.
U.S. Appl. No. 17/237,909, filed Apr. 22, 2021 Non-Final Office Action dated Jul. 27, 2023.
U.S. Appl. No. 17/240,591, filed Apr. 26, 2021 Non-Final Office Action dated Jun. 8, 2023.
U.S. Appl. No. 17/326,017, filed May 20, 2021 Notice of Allowance dated Jul. 3, 2023.
U.S. Appl. No. 17/358,504, filed Jun. 25, 2021 Restriction Requirement dated Jun. 7, 2023.
U.S. Appl. No. 17/360,694, filed Jun. 28, 2021 Restriction Requirement dated Jul. 20, 2023.
U.S. Appl. No. 17/390,682, filed Jul. 30, 2021 Final Office Action dated Jul. 27, 2023.
U.S. Appl. No. 17/392,061, filed Aug. 2, 2021 Non-Final Office Action dated Jul. 17, 2023.
U.S. Appl. No. 16/398,020, filed Apr. 29, 2019 Notice of Allowance dated May 20, 2024.
U.S. Appl. No. 17/234,611, filed Apr. 19, 2021 Non-Final Office Action dated Apr. 23, 2024.
U.S. Appl. No. 17/240,591, filed Apr. 26, 2021 Non-Final Office Action dated Jun. 4, 2024.
U.S. Appl. No. 17/358,504, filed Jun. 25, 2021 Final Office Action dated Mar. 13, 2024.
U.S. Appl. No. 17/358,504, filed Jun. 25, 2021 Notice of Allowance dated Jul. 17, 2024.
U.S. Appl. No. 17/390,682, filed Jul. 30, 2021 Final Office Action dated May 6, 2024.
U.S. Appl. No. 17/390,682, filed Jul. 30, 2021 Non-Final Office Action dated Jul. 5, 2024.
U.S. Appl. No. 17/392,061, filed Aug. 2, 2021 Non-Final Office Action dated Apr. 23, 2024.
U.S. Appl. No. 17/513,789, filed Oct. 28, 2021 Final Office Action dated Jul. 9, 2024.
U.S. Appl. No. 17/554,978, filed Dec. 17, 2021 Non-Final Office Action dated Apr. 19, 2024.
U.S. Appl. No. 17/554,978, filed Dec. 17, 2021 Notice of Allowance dated Jul. 24, 2024.
PCT/US2020/052536 filed Sep. 24, 2020 International Search Report and Written Opinion dated Dec. 4, 2020.
PCT/US2021/014700 filed Jan. 22, 2021 International Search Report and Written Opinion dated Jun. 29, 2021.
PCT/US2021/028018 filed Apr. 19, 2021 International Preliminary Report on Patentability dated Jun. 3, 2022.
PCT/US2021/028018 filed Apr. 19, 2021 International Search Report and Written Opinion dated Sep. 13, 2021.
PCT/US2021/028683 filed Apr. 22, 2021 International Search Report and Written Opinion dated Sep. 16, 2021.
PCT/US2021/029183 filed Apr. 26, 2021 International Search Report and Written Opinion dated Sep. 24, 2021.
PCT/US2021/033443 filed May 20, 2021 International Search Report and Written Opinion dated Sep. 23, 2021.
PCT/US2021/039084 filed Jun. 25, 2021 International Search Report and Written Opinion dated Jan. 10, 2022.
PCT/US2021/044029 filed Jul. 30, 2021 International Search Report and Written Opinion dated Dec. 9, 2021.
PCT/US2021/044223 filed Aug. 2, 2021 International Search Report and Written Opinion dated Dec. 21, 2021.
PCT/US2021/048275 filed Aug. 30, 2021 International Search Report and Written Opinion dated Jan. 4, 2022.
PCT/US2021/064174 filed Dec. 17, 2021 International Search Report and Written Opinion dated May 18, 2022.
PCT/US2021/064642 filed Dec. 21, 2021 International Search Report and Written Opinion dated May 11, 2022.
U.S. Appl. No. 15/008,628, filed Jan. 28, 2016 Final Office Action dated May 30, 2018.
U.S. Appl. No. 15/008,628, filed Jan. 28, 2016 Non-Final Office Action dated Jan. 25, 2019.
U.S. Appl. No. 15/008,628, filed Jan. 28, 2016 Non-Final Office Action dated Nov. 2, 2017.
U.S. Appl. No. 15/008,628, filed Jan. 28, 2016 Notice of Allowance dated May 15, 2019.
U.S. Appl. No. 16/398,020, filed Apr. 29, 2019 Final Office Action dated Jan. 25, 2022.
U.S. Appl. No. 16/398,020, filed Apr. 29, 2019 Non-Final Office Action dated May 11, 2021.
U.S. Appl. No. 17/031,478, filed Sep. 24, 2020 Non-Final Office Action dated May 11, 2022.
PCT/US2021/057135 filed Oct. 28, 2021 International Preliminary Report on Patentability dated May 2, 2023.
PCT/US2021/057135 filed Oct. 28, 2021 International Search Report and Written Opinion dated Mar. 11, 2022.
PCT/US2022/039614 filed Aug. 5, 2022 International Search Report and Written Opinion dated Dec. 22, 2022.
PCT/US2022/044848 filed Sep. 27, 2022 International Search Report and Written Opinion dated Feb. 3, 2023.
PCT/US2022/044879 filed Sep. 27, 2022 International Search Report and Written Opinion dated Mar. 3, 2023.
PCT/US2022/044901 filed Sep. 27, 2022 International Search Report and Written Opinion dated Mar. 3, 2023.
PCT/US2022/044918 filed Sep. 27, 2022 International Search Report and Written Opinion dated Feb. 21, 2023.
PCT/US2022/044923 filed Sep. 27, 2022 International Search Report and Written Opinion dated Feb. 15, 2023.
U.S. Appl. No. 17/156,252, filed Jan. 22, 2021 Notice of Allowance dated Apr. 24, 2023.
U.S. Appl. No. 17/237,909, filed Apr. 22, 2021 Restriction Requirement dated Feb. 1, 2023.
U.S. Appl. No. 17/326,017, filed May 20, 2021 Non-Final Office Action dated Jan. 26, 2023.
U.S. Appl. No. 17/390,682, filed Jul. 30, 2021 Non-Final Office Action dated Mar. 2, 2023.
U.S. Appl. No. 17/392,061, filed Aug. 2, 2021 Restriction Requirement dated Mar. 30, 2023.
U.S. Appl. No. 17/392,061, filed Aug. 2, 2021 Notice of Allowance dated Oct. 27, 2025.
U.S. Appl. No. 17/461,619, filed Aug. 30, 2021 Advisory Action dated Aug. 14, 2025.
U.S. Appl. No. 17/461,619, filed Aug. 30, 2021 Final Office Action dated Jun. 2, 2025.
U.S. Appl. No. 17/461,619, filed Aug. 30, 2021 Non-Final Office Action dated Oct. 7, 2025.
U.S. Appl. No. 17/716,675, filed Apr. 8, 2022 Non-Final Office Action dated Sep. 11, 2025.
U.S. Appl. No. 17/716,675, filed Apr. 8, 2022 Restriction Requirement dated Jul. 2, 2025.
U.S. Appl. No. 17/953,663, filed Sep. 27, 2022 Restriction Requirement dated Oct. 3, 2025.

(56) References Cited

OTHER PUBLICATIONS

U.S. Appl. No. 17/953,860, filed Sep. 27, 2022 Restriction Requirement dated Oct. 22, 2025.
U.S. Appl. No. 17/953,959, filed Sep. 27, 2022 Restriction Requirement dated Oct. 22, 2025.
U.S. Appl. No. 17/954,096, filed Sep. 27, 2022 Non-Final Office Action dated Aug. 26, 2025.
U.S. Appl. No. 17/954,132, filed Sep. 27, 2022 Non-Final Office Action dated Aug. 21, 2025.
U.S. Appl. No. 17/234,611, filed Apr. 19, 2021 Board Decision dated Jan. 23, 2026.
U.S. Appl. No. 17/240,591, filed Apr. 26, 2021 Board Decision dated Feb. 18, 2026.
U.S. Appl. No. 17/390,682, filed Jul. 30, 2021 Notice of Allowance dated Dec. 15, 2025.
U.S. Appl. No. 17/953,663, filed Sep. 27, 2022 Non-Final Office Action dated Jan. 22, 2026.
U.S. Appl. No. 17/953,860, filed Sep. 27, 2022 Non-Final Office Action dated Jan. 29, 2026.
U.S. Appl. No. 17/954,096, filed Sep. 27, 2022 Final Office Action dated Feb. 10, 2026.
U.S. Appl. No. 18/099,185, filed Jan. 19, 2023 Non-Final Office Action dated Dec. 2, 2025.
U.S. Appl. No. 18/372,610, filed Sep. 25, 2023 Notice of Allowance dated Dec. 16, 2025.
U.S. Appl. No. 18/383,814, filed Oct. 25, 2023 Restriction Requirement dated Jan. 22, 2026.
U.S. Appl. No. 17/240,591, filed Apr. 26, 2021 Notice of Allowance dated Mar. 25, 2026.
U.S. Appl. No. 17/461,619, filed Aug. 30, 2021 Final Office Action dated Feb. 10, 2026.
U.S. Appl. No. 17/716,675, filed Apr. 8, 2022 Non-Final Office Action dated Mar. 9, 2026.
U.S. Appl. No. 17/953,959, filed Sep. 27, 2022 Non-Final Office Action dated Mar. 30, 2026.
U.S. Appl. No. 17/954,096, filed Sep. 27, 2022 Notice of Allowance dated Apr. 23, 2026.
U.S. Appl. No. 17/954,132, filed Sep. 27, 2022 Final Office Action dated Mar. 4, 2026.
U.S. Appl. No. 18/075,261, filed Dec. 5, 2022 Non-Final Office Action dated Apr. 22, 2026.
U.S. Appl. No. 18/099,185, filed Jan. 19, 2023 Final Office Action dated Apr. 20, 2026.
U.S. Appl. No. 18/383,814, filed Oct. 25, 2023 Non-Final Office Action dated Apr. 17, 2026.
U.S. Appl. No. 18/593,431, filed Mar. 1, 2024 Non-Final Office Action dated Apr. 21, 2026.

* cited by examiner

RAPIDLY INSERTABLE CENTRAL CATHETER INSERTION ASSEMBLIES AND METHODS

PRIORITY

This application claims the benefit of priority to U.S. Provisional Patent Application No. 63/229,862, filed Aug. 5, 2021, which is incorporated by reference in its entirety into this application.

BACKGROUND

Central venous catheter ("CVCs") are commonly introduced into patients and advanced through their vasculatures by way of the Seldinger technique. The Seldinger technique utilizes a number of steps and medical devices (e.g., a needle, a scalpel, a guidewire, an introducer sheath, a dilator, a CVC, etc.). While the Seldinger technique is effective, the number of steps are time consuming, handling the number of medical devices is awkward, and both of the foregoing can lead to patient trauma. In addition, there is a relatively high potential for touch contamination due to the number of medical devices that need to be interchanged during the Seldinger technique. As such, there is a need to reduce the number of steps and medical devices involved in introducing a catheter such as a CVC into a patient and advancing the catheter through a vasculature thereof.

Disclosed herein are rapidly insertable central catheter ("RICC") insertion assemblies and methods that address the foregoing.

SUMMARY

Disclosed herein is a RICC insertion assembly including, in some embodiments, a RICC, an access guidewire disposed in the RICC, an introducer needle, and a coupler coupling the RICC and the introducer needle together. The introducer needle includes a needle shaft and a sheath over the needle shaft. The needle shaft includes a longitudinal needle slot extending from a proximal portion of the needle shaft through a distal needle tip. The sheath seals the needle slot thereunder except for a portion of the needle slot under a sheath opening in a proximal portion of the sheath. The coupler includes a coupler housing and a valve module disposed in the coupler housing. The valve module seals the proximal portions of the needle shaft and the sheath therein. The access guidewire includes a proximal end coupled to a swivel arm of the coupler and a distal end disposed in the introducer needle. The proximal and distal ends of the access guidewire enforce a loop in the access guidewire. The RICC is disposed over the loop of the access guidewire in a ready-to-deploy state of the RICC insertion assembly.

In some embodiments, the RICC insertion assembly further includes a syringe fluidly coupled to the introducer needle in the ready-to-deploy state of the RICC insertion assembly. The sheath seals the needle slot of the needle shaft thereunder outside of the valve module. The valve module seals the sheath opening of the sheath therein. In addition, the valve module seals around the access guidewire enabling the syringe to aspirate blood.

In some embodiments, the valve module includes an integrated blade disposed in the needle slot under a distal end of the sheath opening. The blade includes a distal facing blade edge configured to cut the sheath off the needle shaft as the introducer needle is withdrawn from the coupler.

Cutting the sheath off the needle shaft allows the access guidewire to escape from the needle shaft by way of the needle slot thereof.

In some embodiments, the coupler housing includes a longitudinal coupler-housing slot configured to allow the access guidewire to escape from the coupler housing when the introducer needle is withdrawn from the coupler.

In some embodiments, the valve module includes separable pieces around the needle shaft and the sheath. The separable pieces are configured to separate and allow the access guidewire to escape from the valve module when the introducer needle is withdrawn from the coupler.

Also disclosed herein is a RICC insertion assembly including, in some embodiments, a RICC, an access guidewire disposed in the RICC, an introducer needle, and a coupler coupling the RICC and the introducer needle together in a ready-to-deploy state of the RICC insertion assembly. The RICC includes a catheter tube, a catheter hub, one or more extension legs, and one or more extension-leg connectors. The catheter hub is coupled to a proximal portion of the catheter tube. Each extension leg of the one-or-more extension legs is coupled to the catheter hub by a distal portion thereof. Each extension-leg connector of the one-or-more extension-leg connectors is over a proximal portion of an extension leg of the one-or-more extension legs. The introducer needle includes a needle shaft, a sheath over the needle shaft, and a needle hub over a proximal portion of the needle shaft and a proximal portion of the sheath. The needle shaft includes a longitudinal needle slot extending from the proximal portion of the needle shaft through a needle tip in a distal portion of the needle shaft. The sheath includes a sheath opening in the proximal portion of the sheath. The coupler includes a coupler housing, a valve module disposed in the coupler housing, and a swivel arm swivelably coupled to the coupler housing. The coupler housing includes a needle-hub receptacle with the needle hub inserted into the needle-hub receptacle. The needle shaft and the sheath extend from the needle hub, through the valve module, and out a distal end of the coupler housing. The swivel arm includes a swivel-arm connector connected to an extension-leg connector of the one-or-more extension-leg connectors. The access guidewire includes a proximal portion including a proximal end and a distal portion including a distal end. The proximal end of the access guidewire is coupled to the swivel-arm connector. The proximal portion of the access guidewire extends along a primary lumen of the RICC. The distal portion of the access guidewire extends along the primary lumen of the RICC, out a distal end of the RICC, into the valve module over the needle hub, into the needle shaft through both the sheath opening and the needle slot, and along a needle lumen of the introducer needle. The distal end of the access guidewire is disposed in the needle lumen just proximal of the needle tip.

In some embodiments, the RICC insertion assembly further includes a syringe fluidly coupled to the introducer needle in the ready-to-deploy state of the RICC insertion assembly. The sheath seals the needle slot of the needle shaft thereunder outside of the valve module. The valve module seals the sheath opening of the sheath therein. And the valve module seals around the access guidewire enabling the syringe to aspirate blood.

In some embodiments, the proximal end of the access guidewire is coupled to the swivel-arm connector and the distal end of the access guidewire is disposed in the needle lumen, thereby enforcing a loop in the access guidewire. The RICC is disposed over the loop of the access guidewire in the ready-to-deploy state of the RICC insertion assembly.

In some embodiments, the swivel arm is configured to flip the loop between a sinistral side of the RICC insertion assembly and a dextral side of the RICC insertion assembly to accommodate both left-handed and right-handed venipunctures with the RICC insertion assembly.

In some embodiments, the coupler includes a needle-hub lock configured to lock the needle hub in the needle-hub receptacle. A pair of lock buttons of the needle-hub lock is distributed between opposing sides of the coupler. The lock buttons are configured to unlock the needle hub when the lock buttons are pressed into the coupler for withdrawal of the introducer needle from the coupler.

In some embodiments, the valve module includes an integrated blade disposed in the needle slot under a distal end of the sheath opening. The blade includes a distal facing blade edge configured to cut the sheath off the needle shaft as the introducer needle is withdrawn from the coupler. Cutting the sheath off the needle shaft allows the access guidewire to escape from the needle shaft by way of the needle slot thereof.

In some embodiments, the coupler housing includes a longitudinal coupler-housing slot configured to allow the access guidewire to escape from the coupler housing when the introducer needle is withdrawn from the coupler.

In some embodiments, the valve module includes separable pieces around the needle shaft and the sheath. The separable pieces are configured to separate and allow the access guidewire to escape from the valve module when the introducer needle is withdrawn from the coupler.

In some embodiments, the catheter tube includes a first section in a distal portion of the catheter tube, a second section in the distal portion of the catheter tube proximal of the first section of the catheter tube, and a tapered junction between the first and second sections of the catheter tube. The first section is formed of a first polymeric material having a first durometer. The second section is formed of a second polymeric material having a second durometer less than the first durometer. The junction has a length between that of exposed portions of the first and second sections of the catheter tube.

In some embodiments, a proximal portion of the first section of the catheter tube is disposed in a bore in a distal portion of the junction and bonded thereto.

In some embodiments, a distal end of the second section of the catheter tube is flush with a proximal end of the junction and bonded thereto.

In some embodiments, the catheter tube possess a column strength sufficient to prevent buckling of the catheter tube when inserted into a needle tract established by a percutaneous puncture with the introducer needle. The column strength is also sufficient to prevent buckling of the catheter tube when advanced through a vasculature of a patient without dilation of tissue about the needle tract or any blood vessels of the vasculature beforehand with a separate dilator.

In some embodiments, the RICC includes a set of three lumens including the primary lumen, a secondary lumen, and a tertiary lumen formed of fluidly connected portions of three catheter-tube lumens, three catheter-hub lumens, and three extension-leg lumens.

In some embodiments, the primary lumen has a primary-lumen aperture in a distal end of the catheter tube, the secondary lumen has a secondary-lumen aperture in a side of the distal portion of catheter tube, and the tertiary lumen has a tertiary-lumen aperture in the side of the distal portion of the catheter tube proximal of the secondary-lumen aperture.

Also disclosed herein is a method for inserting a RICC into a blood-vessel lumen of a patient. The method includes, in some embodiments, insertion assembly-obtaining step, a needle tract-establishing step, an access guidewire-advancing step, an introducer needle-withdrawing step, and a RICC-advancing step. The insertion assembly-obtaining step includes obtaining a RICC insertion assembly. The RICC insertion assembly includes the RICC, an introducer needle including a sheath over a needle shaft, and an access guidewire coupled together by a coupler. A proximal end of the access guidewire is coupled to a swivel arm of the coupler while a distal end of the access guidewire is disposed in the introducer needle by way of a valve module of the coupler. The proximal and distal ends of the access guidewire enforce a loop in the access guidewire as a result. The RICC is disposed over the loop of the access guidewire in a ready-to-deploy state of the RICC insertion assembly. The needle tract-establishing step includes establishing a needle tract from an area of skin to the blood-vessel lumen with the introducer needle. The access guidewire-advancing step includes advancing the distal end of the access guidewire from its initial location in the needle shaft just proximal of a needle tip of the needle shaft into the blood-vessel lumen. The introducer needle-withdrawing step includes withdrawing the introducer needle from the coupler leaving the access guidewire in place in the blood-vessel lumen. The introducer needle includes a longitudinal needle slot extending from a proximal portion of the needle shaft through the needle tip, which allows the access guidewire to escape from the introducer needle with the introducer needle-withdrawing step. The RICC-advancing step includes advancing a catheter tube of the RICC over the access guidewire and into the blood-vessel lumen, thereby inserting the RICC into the blood-vessel lumen.

In some embodiments, the needle tract-establishing step includes flipping the swivel arm and, thus, the loop between a sinistral side of the RICC insertion assembly for a left-handed venipuncture and a dextral side of the RICC insertion assembly for a right-handed venipuncture with the RICC insertion assembly.

In some embodiments, the needle tract-establishing step includes ensuring blood flashes back into a needle hub of the introducer needle, a syringe tip of a syringe fluidly connected to the introducer needle, a barrel of the syringe, or a combination thereof. Ensuring the blood flashes back in accordance with the foregoing confirms the needle tract extends into the blood-vessel lumen.

In some embodiments, the needle tract-establishing step includes drawing a slight vacuum with the syringe while establishing the needle tract such that the blood flashes back into at least the needle hub of the introducer needle upon establishing the needle tract.

In some embodiments, the method further includes a blood-aspirating step. The blood-aspirating step includes aspirating blood with the syringe for confirmation the needle tract extends into the blood-vessel lumen before withdrawing the introducer needle from the coupler in the introducer needle-withdrawing step. The sheath over the needle shaft seals the needle slot thereunder for the blood-aspirating step.

In some embodiments, the valve module is sealed around a distal portion of the access guidewire as well as a sheath opening of the sheath. The sheath opening allows the access guidewire to pass into the needle shaft by way of the needle slot in the ready-to-deploy state of the RICC insertion assembly.

In some embodiments, the introducer needle-withdrawing step includes simultaneously cutting the sheath off the needle shaft with an integrated blade of the valve module while the introducer needle is withdrawn from the coupler.

The cutting of the sheath off the needle shaft allows the access guidewire to escape from the needle shaft by way of the needle slot thereof.

In some embodiments, separable pieces of the valve module around the needle shaft and the sheath in the ready-to-deploy state of the RICC insertion assembly separate to allow the access guidewire to escape from the valve module when the introducer needle is withdrawn from the coupler in the introducer needle-withdrawing step.

In some embodiments, the coupler housing includes a longitudinal coupler-housing slot allowing the access guidewire to escape from the coupler housing when the introducer needle is withdrawn from the coupler in the introducer needle-withdrawing step.

In some embodiments, the method further includes an access guidewire-withdrawing step. The access guidewire-withdrawing step includes withdrawing the access guidewire leaving the catheter tube in place in the blood-vessel lumen.

In some embodiments, the method further includes a maneuver guidewire-advancing step, another RICC-advancing step, and a maneuver guidewire-withdrawing step. The maneuver guidewire-advancing step includes advancing a maneuver guidewire into the blood-vessel lumen by way of a primary lumen of the RICC. The other RICC-advancing step includes advancing a distal portion of the catheter tube farther into the blood-vessel lumen over the maneuver guidewire to a lower ⅓ of a superior vena cava ("SVC") of a heart of the patient. The maneuver guidewire-withdrawing step includes withdrawing the maneuver guidewire leaving the catheter tube in place in the lower ⅓ of the SVC.

These and other features of the concepts provided herein will become more apparent to those of skill in the art in view of the accompanying drawings and following description, which describe particular embodiments of such concepts in greater detail.

DRAWINGS

DESCRIPTION

Figure 1:
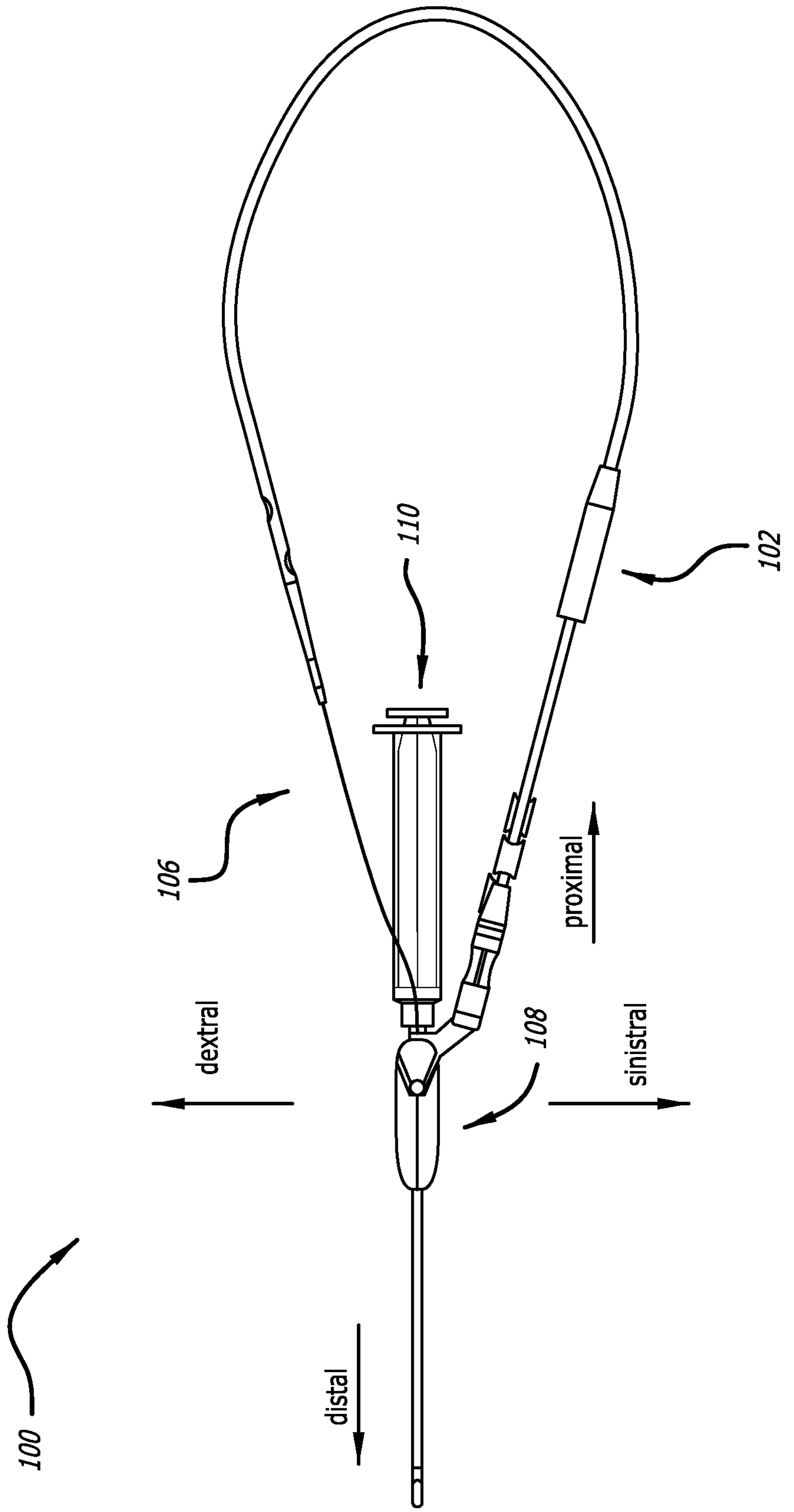
FIG. 1 illustrates a top view of a RICC insertion assembly in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. In addition, any of the foregoing features or steps can, in turn, further include one or more features or steps unless indicated otherwise. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal-end portion" of, for example, a catheter includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal-end portion, or the proximal length of the catheter can include the proximal end of the catheter; however, the proximal portion, the proximal-end portion, or the proximal length of the catheter need not include the proximal end of the catheter. That is, unless context suggests otherwise, the proximal portion, the proximal-end portion, or the proximal length of the catheter is not a terminal portion or terminal length of the catheter.

With respect to "distal," a "distal portion" or a "distal-end portion" of, for example, a catheter includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal-end portion, or the distal length of the catheter can include the distal end of the catheter; however, the distal portion, the distal-end portion, or the distal length of the catheter need not include the distal end of the catheter. That is, unless context suggests otherwise, the distal portion, the distal-end portion, or the distal length of the catheter is not a terminal portion or terminal length of the catheter.

Unless defined otherwise, all technical and scientific terms used herein have the same meaning as commonly understood by those of ordinary skill in the art.

As set forth above with respect to the Seldinger technique, the number of steps are time consuming, handling the number of medical devices is awkward, and both of the foregoing can lead to patient trauma. In addition, there is a relatively high potential for touch contamination due to the number of medical devices that need to be interchanged during the Seldinger technique. As such, there is a need to reduce the number of steps and medical devices involved in introducing a catheter such as a CVC into a patient and advancing the catheter through a vasculature thereof.

Disclosed herein are RICC insertion assemblies and methods that address the foregoing need. For example, a RICC insertion assembly can include a RICC, an access guidewire, an introducer needle, and a coupler coupling the foregoing components together. The introducer needle can include a needle shaft and a sheath. The needle shaft can include a longitudinal needle slot. The sheath can seal the needle slot thereunder except for a sheath opening thereto in a proximal portion of the sheath. The coupler can include a coupler housing and a valve module disposed in the coupler housing. The valve module can seal the needle shaft and the sheath therein. The access guidewire can include a proximal end coupled to the coupler and a distal end disposed in the needle shaft, thereby enforcing a loop in the access guidewire. The RICC can be disposed over the loop in a ready-to-deploy state of the RICC insertion assembly.

The foregoing features as well as other features of the RICC insertion assemblies and methods provided herein will become more apparent to those of skill in the art in view of the accompanying drawings and following description, which describe particular embodiments of the RICC insertion assemblies and methods in greater detail. However, it should be understood the RICCs of the RICC insertion assemblies are but one type of catheter that can be incorporated into catheter insertion assemblies like those provided herein. Indeed, peripherally inserted central catheters ("PICCs"), dialysis catheters, or the like can also be incorporated into catheter insertion assemblies and methods.

RICC Insertion Assemblies

Figure 2:
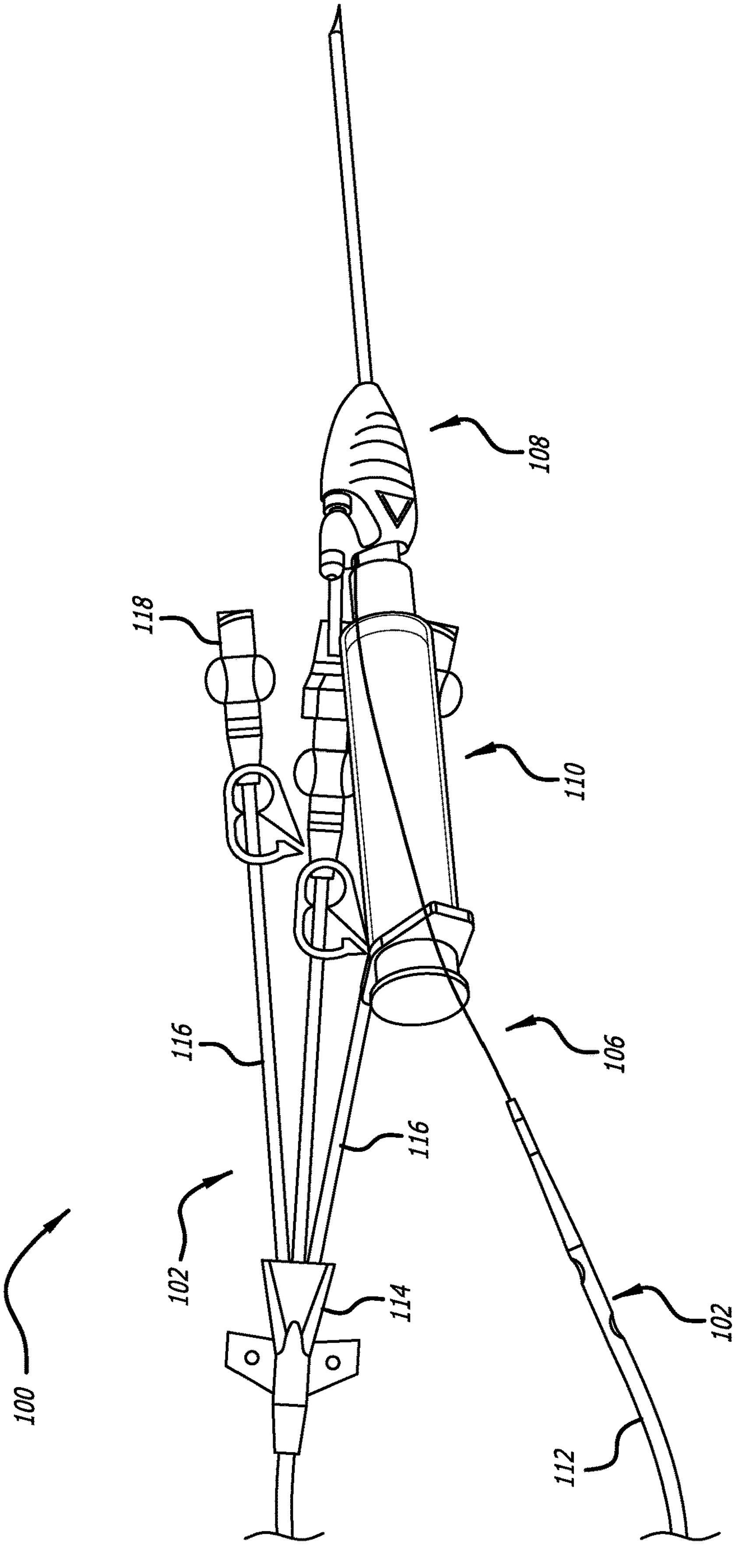
FIG. 2 illustrates a perspective view of the RICC insertion assembly in accordance with some embodiments.
Figure 3:
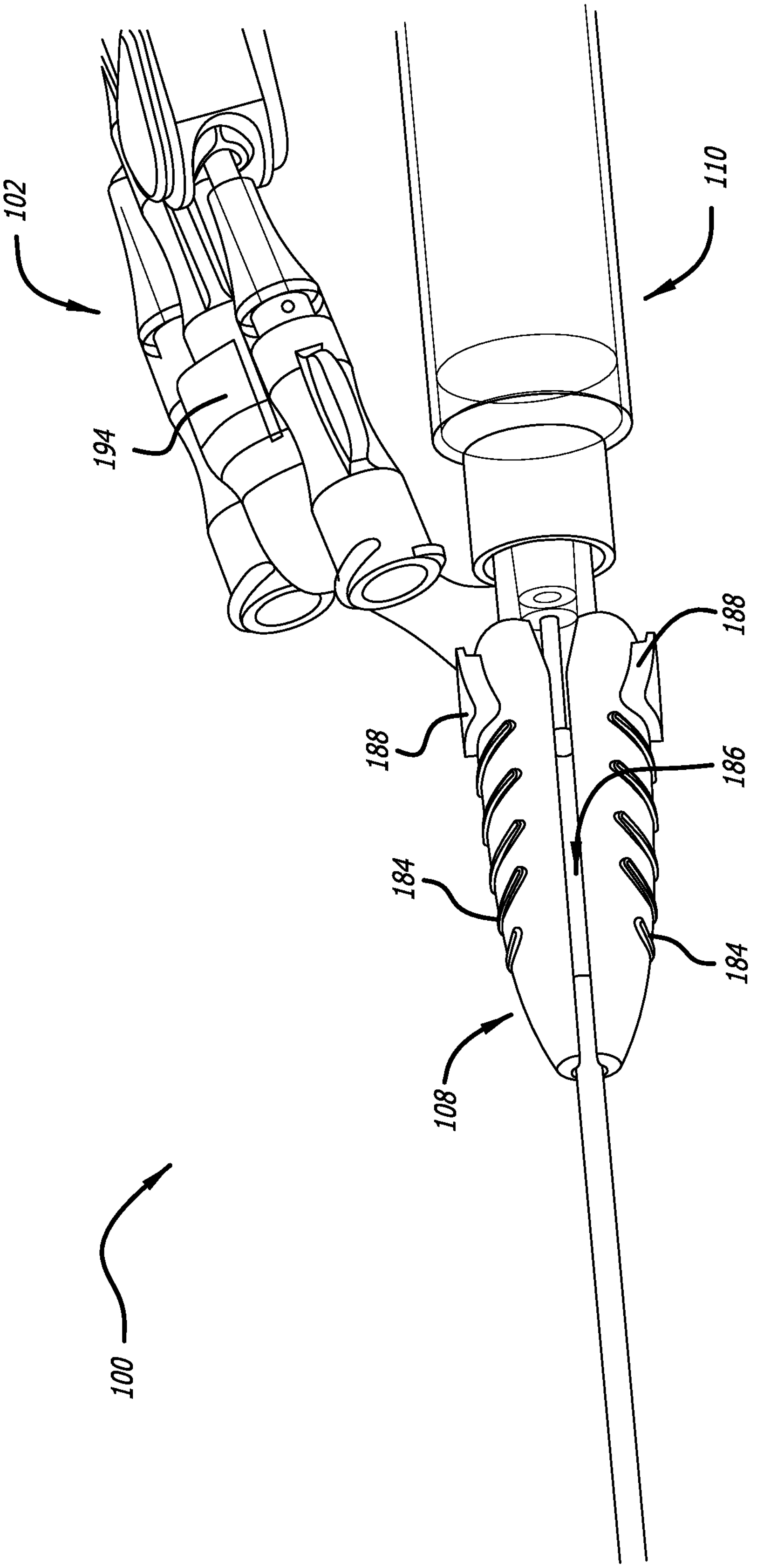
FIG. 3 illustrates a bottom view of the RICC insertion assembly in accordance with some embodiments.
Figure 4:
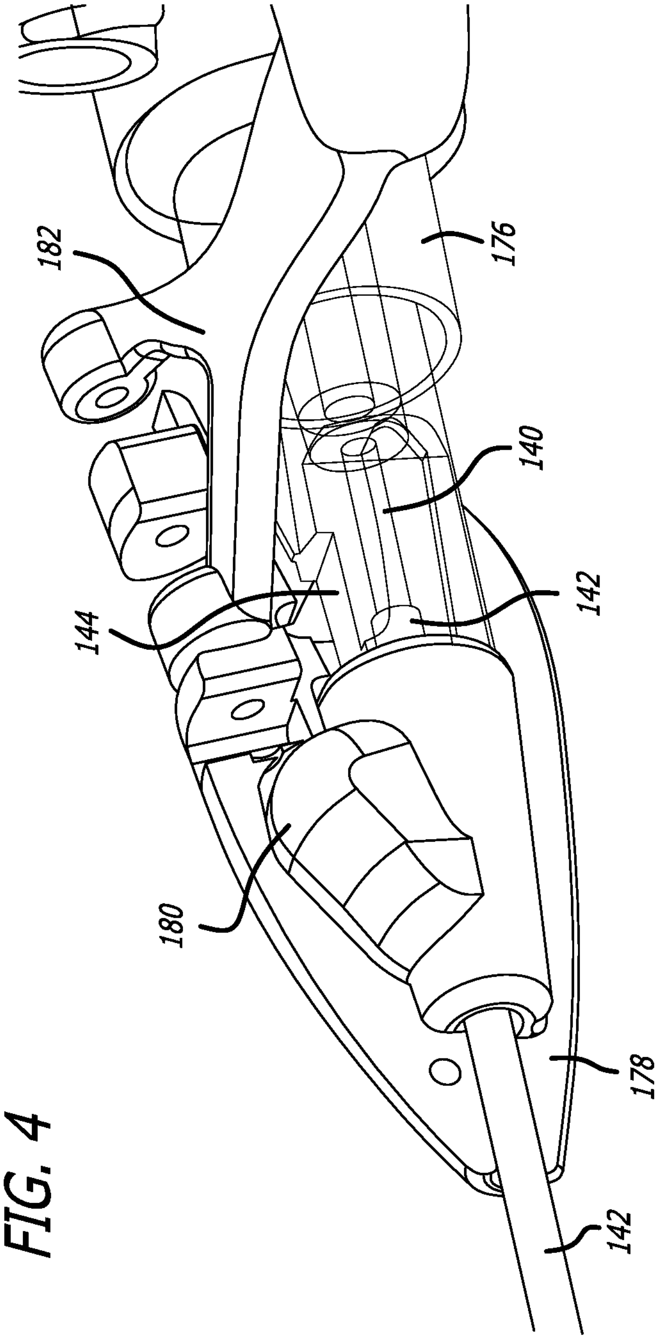
FIG. 4 illustrates a cutaway view of a coupler of the RICC insertion assembly in accordance with some embodiments.
Figure 5:
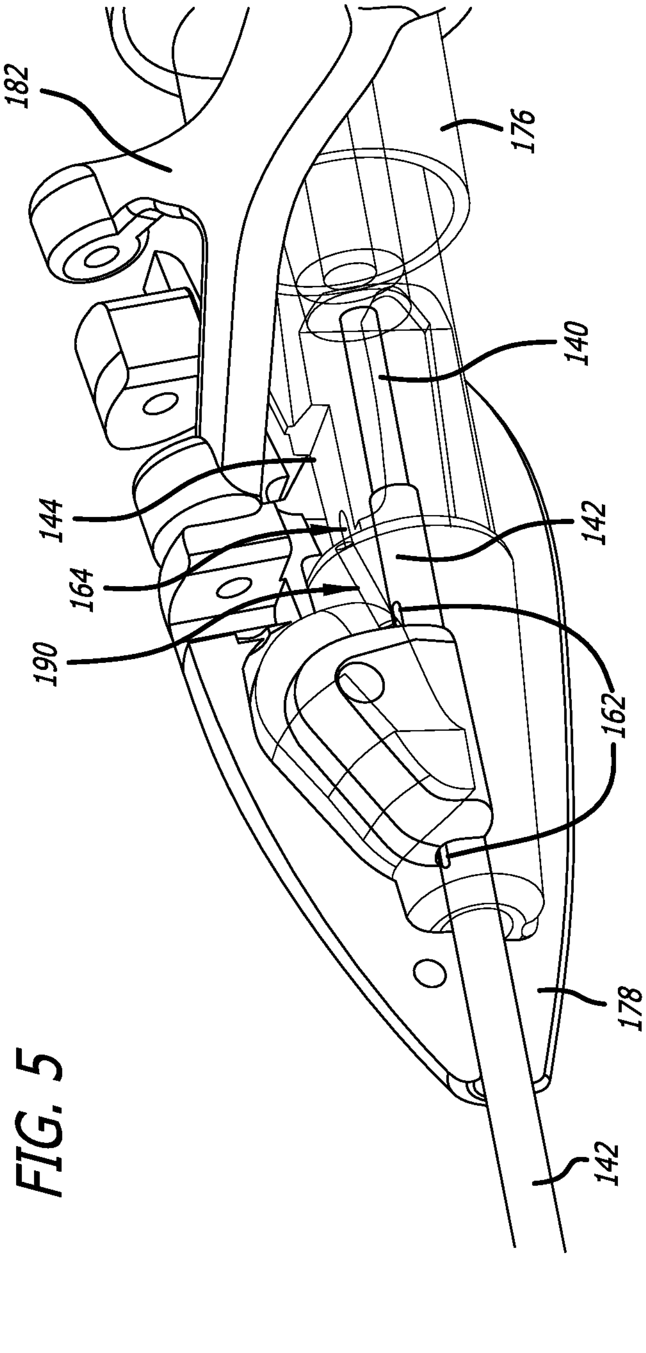
FIG. 5 illustrates another cutaway view of the coupler in accordance with some embodiments.
Figure 6:
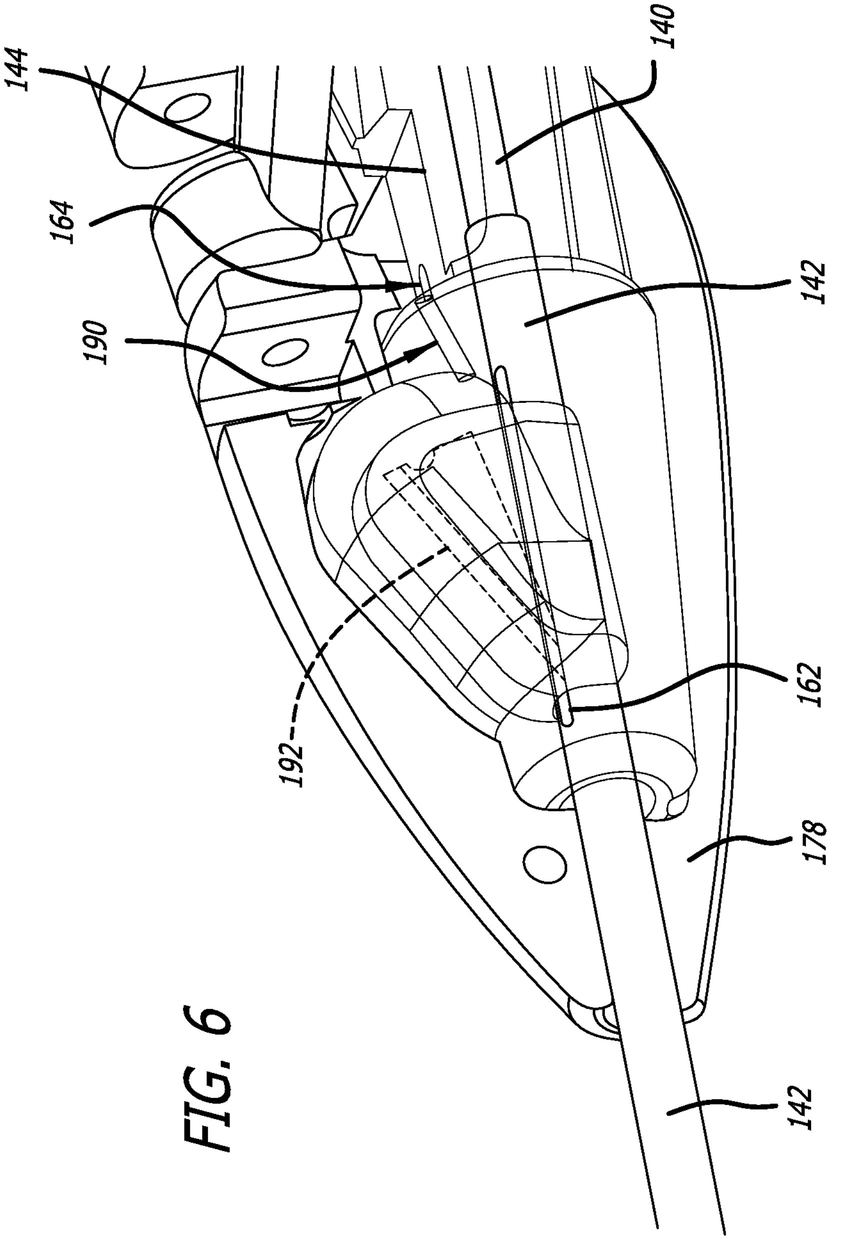
FIG. 6 illustrates yet another cutaway view of the coupler in accordance with some embodiments.
Figure 7:
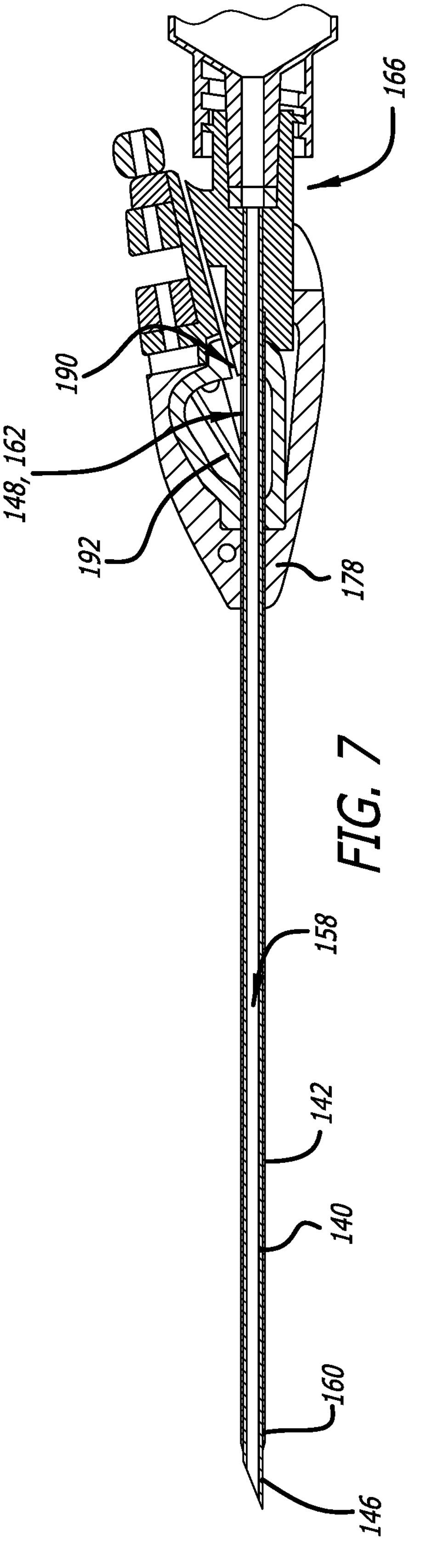
FIG. 7 illustrates a longitudinal cross section of the coupler and an introducer needle of the RICC insertion assembly in accordance with some embodiments.

FIGS. 1-3 illustrate various views of a RICC insertion assembly 100 in accordance with some embodiments.

As shown, the RICC insertion assembly 100 includes a RICC 102, an introducer needle 104, an access guidewire 106, and a coupler 108 coupling the RICC 102, the introducer needle 104, and the access guidewire 106 together in a ready-to-deploy state of the RICC insertion assembly 100. Notably, the proximal end of the access guidewire 106 is coupled to the coupler 108 and the distal end of the access guidewire 106 is disposed in the needle lumen 158 of the introducer needle 104 as set forth below. This enforces a loop in the access guidewire 106, which loop the RICC 102 is disposed over in the ready-to-deploy state of the RICC insertion assembly 100 keeping the RICC insertion assembly 100 in a relatively compact form.

The RICC insertion assembly 100 can further include a syringe 110 fluidly coupled to the introducer needle 104 in the ready-to-deploy state of the RICC insertion assembly 100. As set forth below, the sheath 142 seals the needle slot 148 of the needle shaft 140. In particular, the sheath 142 seals the needle slot 148 outside of the valve module 180. The valve module 180, in turn, seals over the sheath opening 162 of the sheath 142 that opens to the needle slot 148. The valve module 180 also seals around the access guidewire 106. Such seals enable the syringe 110 to aspirate blood in accordance with the blood-aspirating step of the method set forth below.

Figure 12:
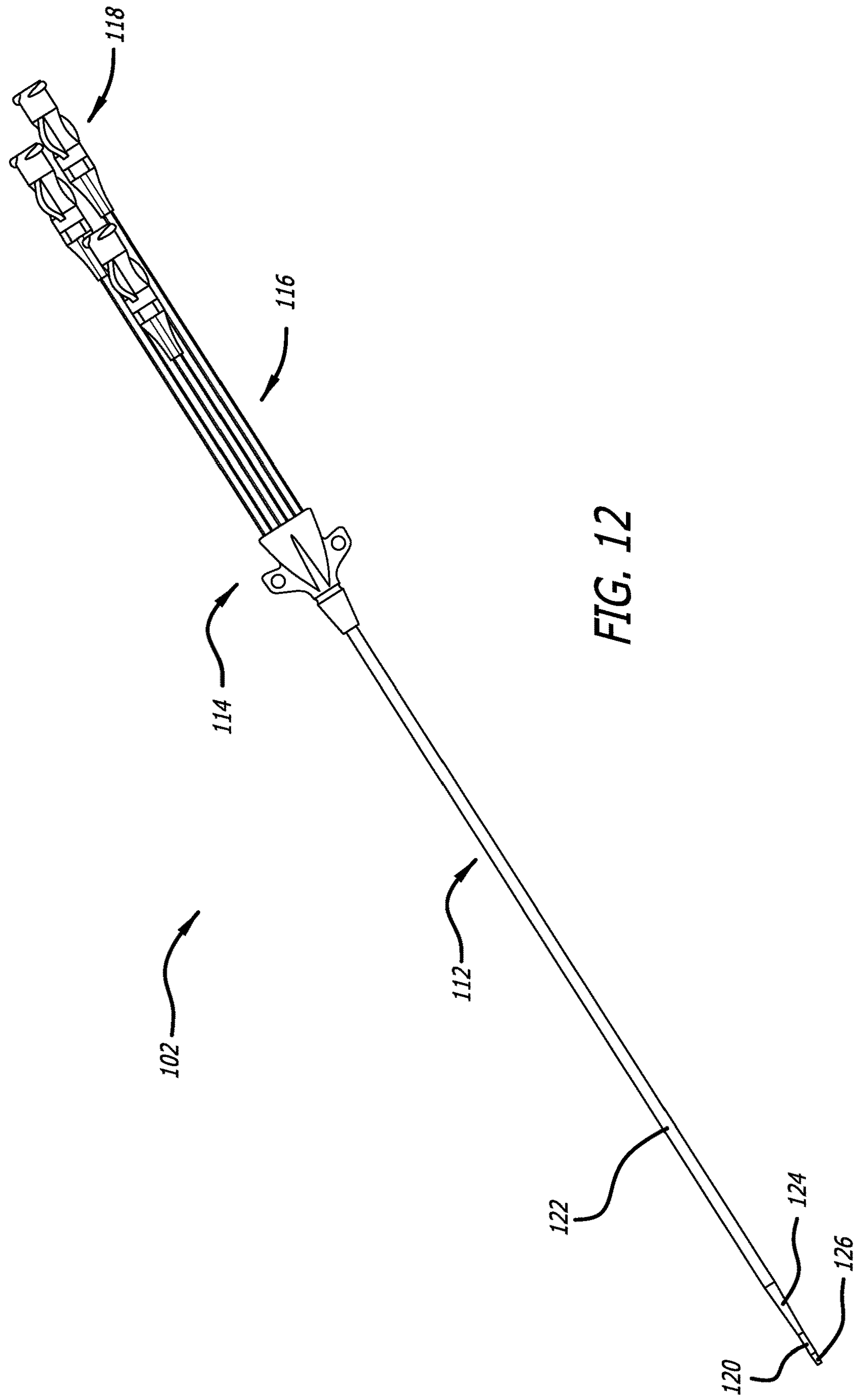
FIG. 12 illustrates a RICC of the RICC insertion assembly in accordance with some embodiments.
Figure 13:
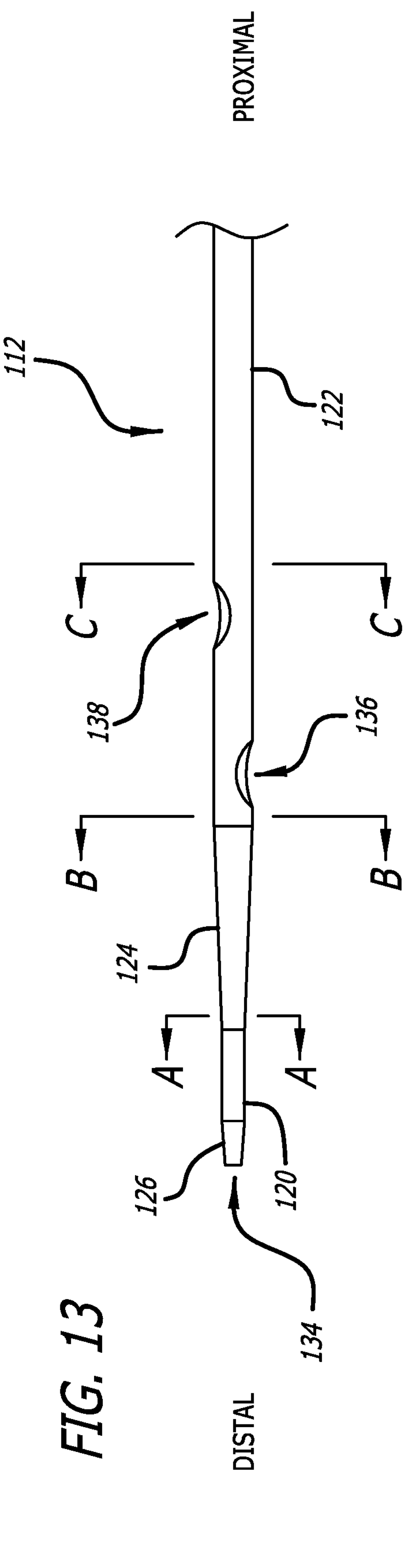
FIG. 13 illustrates a detailed view of a distal portion of a catheter tube of the RICC in accordance with some embodiments.

FIG. 12 illustrates the RICC 102 of the RICC insertion assembly 100 in accordance with some embodiments.

As shown, the RICC 102 includes a catheter tube 112, a catheter hub 114, one or more extension legs 116, and one or more extension-leg connectors 118.

FIGS. 13-16 illustrate various views of the catheter tube 112 of the RICC 102 in accordance with some embodiments.

The catheter tube 112 includes a first section 120 in a distal portion of the catheter tube 112, a second section 122 in the distal portion of the catheter tube 112 proximal of the first section 120, and a tapered junction 124 between the first and second sections 120 and 122 of the catheter tube 112.

Figure 16:
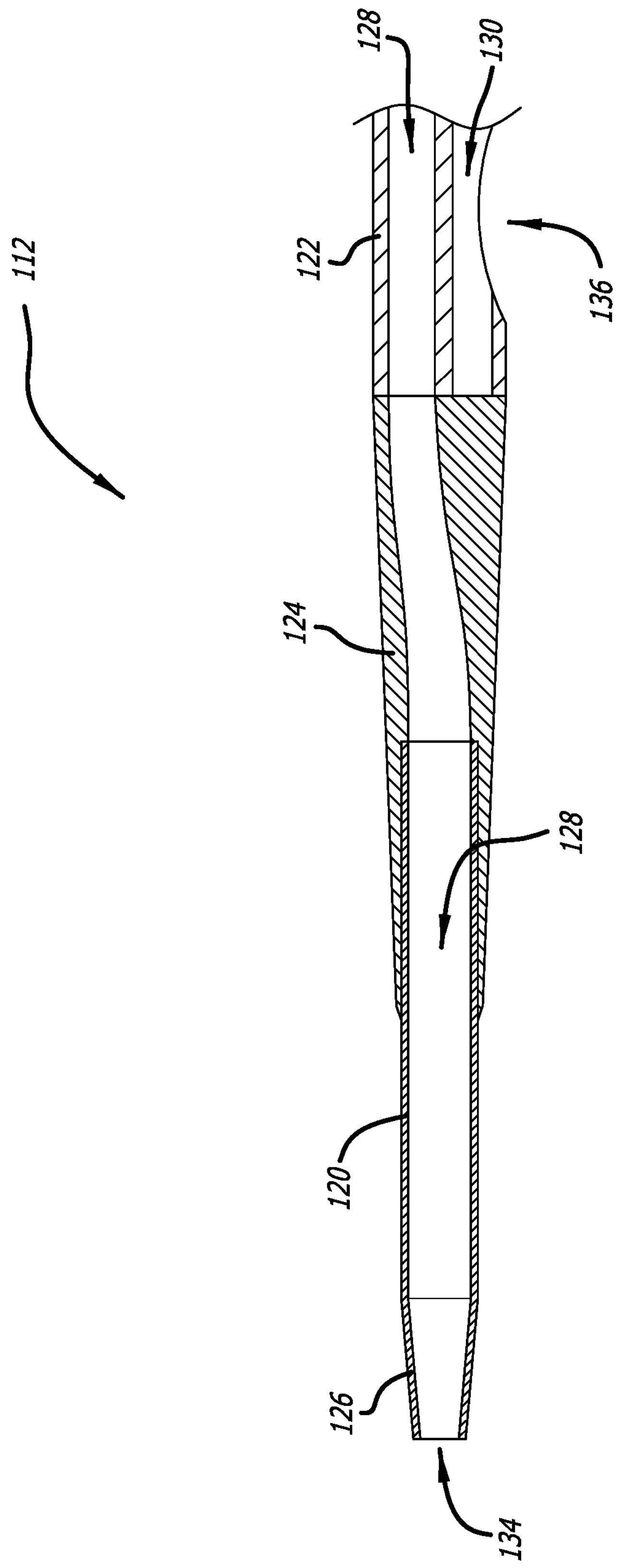
FIG. 16 illustrates a longitudinal cross section of the distal portion of the catheter tube in accordance with some embodiments.

The first section 120 of the catheter tube 112 includes a catheter tip 126 having a relatively short taper from an outer diameter of a distal portion of the first section 120 distal of the junction 124 to an outer diameter of a distal end of the first section 120. The taper of the catheter tip 126 is configured for immediate dilation of tissue about a needle tract established with the introducer needle 104 up to the outer diameter of the distal portion of the first section 120 of the catheter tube 112. As best shown in FIG. 16, the first section 120 of the catheter tube 112 also includes a proximal portion disposed in a bore of a distal portion of the junction 124 and fixedly coupled thereto such as by a solvent bond, an adhesive bond, or a heat weld.

The second section 122 of the catheter tube 112 includes a consistent outer diameter over its length from a distal end of the second section 122 to a proximal end of the second section 122. The consistent diameter of the second section 122 of the catheter tube 112 is configured for smooth insertion into the needle tract and targeted vasculature subsequent to any dilation by the first section 120 of the catheter tube 112 and the junction 124. The distal end of the second section 122 of the catheter tube 112 has a flat face flush with the flat-faced proximal end of the junction 124 and fixedly coupled thereto such as by a solvent bond, an adhesive bond, or a heat weld.

The junction 124 includes a taper over its length from a proximal end of the junction 124 to a distal end of the junction 124. The taper of the junction 124 is configured for immediate dilation of the tissue about the needle tract from the outer diameter of the proximal portion of the first section 120 of the catheter tube 112 to the outer diameter of the second section 122 of the catheter tube 112. An abluminal surface of the junction 124 smoothly transitions from an abluminal surface of the first section 120 of the catheter tube 112 to an abluminal surface of the second section 122 of the catheter tube 112 without edges that catch on skin when the catheter tube 112 is inserted into the needle tract. In addition to the edges being minimal to negligible, the edges can include solvent-interdiffused polymeric material of the polymeric materials from which the catheter tube 112 is formed, which smoothens the transitions from the first section 120 of the catheter tube 112 to the junction 124 and from the junction 124 to the second section 122 of the catheter tube 112. Notably, the junction 124 has a length approximately commensurate with a length of an exposed portion of the first section 120 of the catheter tube 112 or between lengths of exposed portions of the first and second sections 120 and 122 of the catheter tube 112. As such, the length of the exposed portion of the first section 120 of the catheter tube 112 is less than the length of the junction 124 up to approximately commensurate with the length of the junction 124.

The first section 120 of the catheter tube 112 is formed of a first polymeric material (e.g., a polytetrafluoroethylene, a polypropylene, or a polyurethane) having a first durometer. The second section 122 of the catheter tube 112 is formed of a second polymeric material (e.g., a polyvinyl chloride, a polyethylene, another polyurethane, or a silicone) having a second durometer less than the first durometer. For example, the first section 120 of the catheter tube 112 can be formed of a first polyurethane having the first durometer while the second section 122 of the catheter tube 112 can be formed of a second, different polyurethane (e.g., a same or different diisocyanate or triisocyanate reacted with a different diol or triol, a different diisocyanate or triisocyanate reacted with a same or different diol or triol, a same diisocyanate or triisocyanate reacted with a same diol or triol under different conditions or with different additives, etc.) having the second durometer less than the first durometer. Indeed, polyurethanes are advantageous for the catheter tube 112 in that polyurethanes can be relatively rigid at room-temperature but become more flexible in vivo at body temperature, which reduces irritation to vessel walls as well as phlebitis. Polyurethanes are also advantageous in that they can be less thrombogenic than some other polymers. The junction 124 is formed of the second polymeric material or a third polymeric material (e.g., yet another polyurethane) having a third durometer less than the first durometer and greater than, approximately equal to, or less than the second durometer.

It should be understood the first durometer of the first polymeric material, the second durometer of the second polymeric material, and the third durometer of the third polymeric material can be on different scales (e.g., Type A or Type D). With this understanding, the second durometer of the second polymeric material or the third durometer of the third polymeric material might not be numerically less than the first durometer of the first polymeric material when the second durometer or the third durometer is less than the first durometer. Indeed, the hardness of the second polymeric material or the third polymeric material can still be less than the hardness of the first polymeric material as the different scales—each of which ranges from 0 to 100—are designed for characterizing different materials in groups of the materials having a like hardness.

In accordance with the first section 120 of the catheter tube 112, the second section 122 of the catheter tube 112, and the junction 124 between the first and second sections 120 and 122 of the catheter tube 112 set forth above, the catheter tube 112 possesses a column strength sufficient to prevent buckling of the catheter tube 112 when inserted into a needle tract established by with the introducer needle 104. The column strength of the catheter tube 112 is also sufficient to prevent buckling of the catheter tube 112 when advanced through a vasculature of a patient without dilation of tissue about the needle tract or any blood vessels of the vasculature beforehand with a separate dilator.

Figure 14:
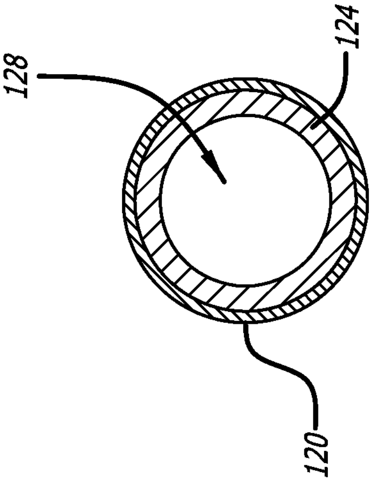
FIG. 14 illustrates a transverse cross section of the distal portion of the catheter tube in accordance with some embodiments.
Figure 15:
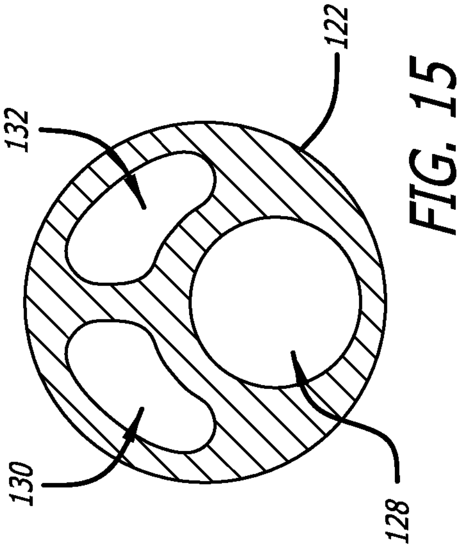
FIG. 15 illustrates another transverse cross section of the distal portion of the catheter tube in accordance with some embodiments.

The catheter tube 112 includes one or more catheter-tube lumens extending through the catheter tube 112; however, only one catheter-tube lumen typically extends from a proximal end of the catheter tube 112 to a distal end of the catheter tube 112 in a multiluminal RICC (e.g., a diluminal RICC, a triluminal RICC, a tetraluminal RICC, a pentaluminal RICC, a hexaluminal RICC, etc.). (See FIGS. 13-16.) Indeed, the first section 120 of the catheter tube 112 typically includes a single lumen therethrough as shown in FIGS. 14 and 16.

The catheter hub 114 is coupled to a proximal portion of the catheter tube 112. The catheter hub 114 includes one or more catheter-hub lumens corresponding in number to the one-or-more catheter-tube lumens. The one-or-more catheter-hub lumens extends through an entirety of the catheter hub 114 from a proximal end of the catheter hub 114 to a distal end of the catheter hub 114.

Each extension leg of the one-or-more extension legs 116 is coupled to the catheter hub 114 by a distal portion thereof. The one-or-more extension legs 116 respectively include one or more extension-leg lumens, which, in turn, correspond in number to the one-or-more catheter-hub lumens. Each extension-leg lumen of the one-or-more extension-leg lumens extends through an entirety of the extension leg from a proximal end of the extension leg to a distal end of the extension leg.

Each extension-leg connector of the one-or-more extension-leg connectors 118 is over a proximal portion of an extension leg of the one-or-more extension legs 116. For example, each extension-leg connector of the one-or-more extension-leg connectors 118 can be a Luer connector over a proximal portion of an extension leg of the one-or-more extension legs 116. Through such an extension-leg connector, a corresponding extension leg and the extension-leg lumen thereof can be connected to another medical device and a lumen thereof. However, in the ready-to-deploy state of the RICC insertion assembly 100 at least one extension-leg connector (e.g., the extension-leg connector including part of the primary lumen 128 of the RICC 102) is connected to the swivel-arm connector 194 of the swivel arm 182 of the coupler 108 to enforce the loop in the access guidewire 106 and the RICC 102 thereover.

As shown, the RICC 102 is a triluminal RICC including a set of three lumens; however, the RICC 102 is not limited to the set of the three lumens as set forth above. The set of three lumens includes a primary lumen 128, a secondary lumen 130, and a tertiary lumen 132 formed of fluidly connected portions of three catheter-tube lumens, three catheter-hub lumens, and three extension-leg lumens. The primary lumen 128 has a primary-lumen aperture 134 in the distal end of the first section 120 of the catheter tube 112, which corresponds to the distal end of the catheter tube 112 and a distal end of the RICC 102. The secondary lumen 130 has a secondary-lumen aperture 136 in a side of the distal portion of the catheter tube 112. The tertiary lumen 132 has a tertiary-lumen aperture 138 in the side of the distal portion of the catheter tube 112 proximal of the secondary-lumen aperture 136.

FIGS. 7-11 illustrate various views of the introducer needle 104 of the RICC insertion assembly 100 in accordance with some embodiments.

As shown, the introducer needle 104 includes a needle shaft 140, a sheath 142 over the needle shaft 140, and a needle hub 144 over both a proximal portion of the needle shaft 140 and a proximal portion of the sheath 142. In at least the ready-to-deploy state of the RICC insertion assembly 100, the needle shaft 140 and the sheath 142 extend from the needle hub 144, through the valve module 180, and out a distal end of the coupler housing 178.

The needle shaft 140 includes a needle tip 146 in a distal portion of the needle shaft 140 and a longitudinal needle slot 148 extending from the proximal portion of the needle shaft 140 through the needle tip 146.

The needle tip 146 includes a bevel having a tip bevel 152 and a primary bevel 154 proximal of the tip bevel 152. A tip-bevel angle of the tip bevel 152 is greater than a primary-bevel angle of the primary bevel 154 such that the bevel provides a smooth transition over the needle tip 146. Such a needle tip is thusly configured for establishing a needle tract from an area of skin into a blood-vessel lumen of a patient in accordance with the needle tract-establishing step of the method set forth below.

The needle slot 148 extends from the proximal portion of the needle shaft 140 through the needle tip 146, thereby forming a needle channel 156 along a majority of a length of the needle shaft 140 as opposed to a needle lumen therethrough. The needle slot 148 has a width sized in accordance with an outer diameter of the access guidewire 106, which allows the access guidewire 106 to pass from the proximal portion of the needle shaft 140 through the needle tip 146 when the introducer needle-withdrawing step of the method set forth below is performed.

While the needle shaft 140 includes the foregoing needle slot 148, it should be understood the introducer needle 104 includes a needle lumen 158; however, the needle lumen 158 results from the combination of the needle shaft 140 and the sheath 142 over the needle shaft 140. Indeed, the sheath 142 over the needle shaft 140 seals the needle slot 148 thereunder forming the needle lumen 158 of the introducer needle 104 and enabling the syringe 110 to aspirate blood in accordance with the blood-aspirating step of the method set forth below.

The sheath 142 includes a sheath tip 160 in a distal portion of the sheath 142 and a sheath opening 162 in a side of the proximal portion of the sheath 142.

The sheath tip 160 includes a relatively short taper from an outer diameter of the distal portion of the sheath 142 to an outer diameter of a distal end of the sheath 142, the latter of which is commensurate with an outer diameter of the distal portion of the needle shaft 140. The taper has a taper angle less than the primary-bevel angle of the primary bevel 154 of the needle tip 146, which, in turn, is less than the tip-bevel angle of the tip bevel 152 of the needle tip 146. The sheath tip 160 including such a taper is configured to provide a smooth transition from the needle tip 146 to the sheath body for the needle tract-establishing step of the method set forth below.

The sheath opening 162 opens to the needle slot 148 of the needle shaft 140 allowing the access guidewire 106 to pass through the sheath opening 162 and into the needle slot 148 in the ready-to-deploy state of the RICC insertion assembly 100. Thus, the sheath opening 162 has a width approximately commensurate with a width of the needle slot 148, which, in turn, is sized in accordance with the diameter of the access guidewire 106. The sheath opening 162 also has a length sufficient to allow the access guidewire 106 to pass through the sheath opening 162 and into the needle slot 148 while also accommodating the blade 192 of the valve module 180 under a distal end of the sheath opening 162. Notably, the sheath 142 over the needle shaft 140 seals the needle slot 148 thereunder except for that under the sheath opening 162. However, the valve module 180 seals over the needle slot 148 exposed by the sheath opening 162 by sealing the proximal portions of the needle shaft 140 and the sheath 142 therein, thereby enabling the syringe 110 to aspirate blood in accordance with the blood-aspirating step of the method set forth below.

The sheath 142, or a sheath body thereof, is formed of a polymeric material configured to facilitate a smooth, consistent insertion of the introducer needle 104 from an area of skin to a blood-vessel lumen of a patient in accordance with the needle tract-establishing step of the method set forth below. In addition, the polymeric material has mechanical properties at a thickness of the sheath 142 sufficient to withstand collapse of the sheath 142 into the needle slot 148 of the needle shaft 140 when the blood-aspirating step of the method set forth below is performed, notably, while also facilitating the cutting of the sheath 142 off the needle shaft 140 in accordance with the introducer needle-withdrawing step of the method set forth below. Such a polymeric material can include, but is not limited to, polyethylene, polypropylene, or polytetrafluoroethylene.

The needle hub 144 includes an access-guidewire channel 164 in a distal portion of the needle hub 144 and a needle-hub connector 166 in a proximal portion of the needle hub 144.

The access-guidewire channel 164 of the needle hub 144 is configured to allow the access guidewire 106 to pass over the needle hub 144 and direct the access guidewire 106 into the access-guidewire conduit 190 of the valve module 180. The access-guidewire channel 164 is open such that the access guidewire 106 lies in the access-guidewire channel 164 in at least the ready-to-deploy state of the RICC insertion assembly 100. Advantageously, the open access-guidewire channel 164 allows the access guidewire 106 to remain in place when the introducer needle 104 is withdrawn from the RICC insertion assembly 100 in accordance with the introducer needle-withdrawing step of the method set forth below.

The needle-hub connector 166 includes a needle-hub bore 168 and an optional needle-hub flange 170 about the needle-hub connector 166.

The needle-hub bore 168 of the needle-hub connector 166 is configured to accept a syringe tip 172 of the syringe 110 therein for fluidly connecting the introducer needle 104 to the syringe 110. Indeed, the needle-hub bore 168 can have a Luer taper (e.g., a 6% taper) configured to accept the syringe tip 172 therein, which syringe tip 172 can be complementarily configured with a Luer taper.

The needle-hub flange 170 of the needle-hub connector 166 is configured to screw together with internal threads 174 of a threaded collar 176 around the syringe tip 172 of the syringe 110. While the threaded collar 176 of the syringe 110 is optional, the needle-hub flange 170 advantageously provides a so-called Luer lock-style connection with the internal threads 174 of the threaded collar 176 when both are present. This provides added security against inadvertent disconnection of the introducer needle 104 and the syringe 110 over that provided by an otherwise Luer slip-style connection.

FIGS. 4-8 illustrate various view of the coupler 108 of the RICC insertion assembly 100 in accordance with some embodiments.

As shown, the coupler 108 includes a coupler housing 178, a valve module 180 disposed in the coupler housing 178, and a swivel arm 182 swivelably coupled to the coupler housing 178.

The coupler housing 178 includes two molded halves coupled together to form an ovoid body configured to be comfortably held underhand (e.g., cradled) or overhand in either a left hand for a left-handed venipuncture or a right hand for a right-handed venipuncture with the RICC insertion assembly 100. To further facilitate such venipunctures, an outside of each half of the two molded halves can be textured as shown with grip-enhancing arcuate ridges 184 or the like. An inside of each half of the two molded halves includes depressions that form a valve-module compartment and a needle-hub receptacle when the two molded halves are coupled together as shown. (See FIGS. 4-8, which include the valve module 180 disposed in a depression of a molded half of the two molded halves that form the valve-module compartment. FIGS. 4-8 also include the needle hub 144 of the introducer needle 104 disposed in a depression of the molded half of the two molded halves that form the needle-hub receptacle.) In addition, each half of the two molded halves includes a lock-button through hole for a corresponding lock button of the pair of lock buttons 188 of the needle-hub lock. (See FIG. 3 for the lock buttons 188 extending through the corresponding pair of lock-button through holes.) Notably, the coupler housing 178 includes a longitudinal coupler-housing slot 186 formed between the two molded halves. The couple-housing slot is configured to allow the access guidewire 106 to escape from the coupler housing 178 when the introducer needle 104 is withdrawn from the coupler 108 in the introducer needle-withdrawing step of the method set forth below.

The valve-module compartment is configured to hold the valve module 180 therein. Indeed, the valve-module compartment includes the valve module 180 disposed therein in the ready-to-deploy state of the RICC insertion assembly 100. Notably, the valve-module compartment is further configured with sufficient space to allow the separable pieces of the valve module 180 set forth below to separate for the escape of the access guidewire 106 when the introducer needle 104 is withdrawn from the coupler 108 in the introducer needle-withdrawing step of the method set forth below.

The needle-hub receptacle is configured to hold the needle hub 144 of the introducer needle 104 therein. Indeed, the needle-hub receptacle includes the needle hub 144 inserted therein in the ready-to-deploy state of the RICC insertion assembly 100. Notably, a needle-hub lock configured to lock the needle hub 144 in the needle-hub receptacle is positioned about the needle-hub receptacle. A pair of lock buttons 188 (e.g., spring-loaded lock buttons) of the needle-hub lock is distributed between opposing sides of the coupler 108, particularly in the lock-button through holes of the two molded halves of the coupler housing 178 such that each lock button of the lock buttons 188 extends through the coupler housing 178 on its respective side of the coupler 108. The lock buttons 188 are configured to unlock the needle hub 144 when the lock buttons 188 are pressed into the coupler 108 for withdrawal of the introducer needle 104 from the coupler 108 in the introducer needle-withdrawing step of the method set forth below.

The valve module 180 includes an access-guidewire conduit 190, an integrated blade 192, and a number of separable pieces.

The access-guidewire conduit 190 is configured to direct the access guidewire 106 from the access-guidewire channel 164 of the needle hub 144 into both the sheath opening 162 of the sheath 142 and the needle slot 148 of the needle shaft 140 thereunder. Indeed, the access-guidewire conduit 190 includes the access guidewire 106 disposed therein in the ready-to-deploy state of the RICC insertion assembly 100. Notably, the valve module 180 seals around the access guidewire 106 in the access-guidewire conduit 190 such that the syringe 110 is able to aspirate blood in accordance with the blood-aspirating step of the method set forth below.

The blade 192 extends from an attachment point in the valve module 180 into the needle slot 148 of the needle shaft 140 such that the blade 192 is disposed in the needle slot 148 under the distal end of the sheath opening 162 of the sheath 142. The blade 192 includes a distal facing blade edge configured to cut the sheath 142 off the needle shaft 140 as the introducer needle 104 is withdrawn in a proximal direction from the coupler 108 in the introducer needle-withdrawing step of the method set forth below. Cutting the sheath 142 off the needle shaft 140 allows the access guidewire 106 to escape from the needle shaft 140 by way of the needle slot 148.

The separable pieces of the valve module 180 are disposed around the needle shaft 140 and the sheath 142 in the ready-to-deploy state of the RICC insertion assembly 100. For example, the separable pieces of the valve module 180 can be separable halves of the valve module 180 disposed around the needle shaft 140 and the sheath 142. The separable pieces of the valve module 180 are configured to separate and allow the access guidewire 106 to escape from the valve module 180 when the introducer needle 104 is withdrawn from the coupler 108 in the introducer needle-withdrawing step of the method set forth below.

The swivel arm 182 includes a swivel-arm connector 194 connected to an extension-leg connector of the one-or-more extension-leg connectors 118 in the ready-to-deploy state of the RICC insertion assembly 100. While not shown, the swivel-arm connector 194 includes an access-guidewire attachment point within the swivel-arm connector 194 to which the proximal end of the access guidewire 106 is attached in the ready-to-deploy state of the RICC insertion assembly 100. In combination with the distal end of the access guidewire 106 being disposed in the needle lumen 158 of the introducer needle 104, the loop in the access guidewire 106 set forth above is enforced. Advantageously, the swivel arm 182 is configured to flip the loop—or at least the one-or-more extension legs 116 of the RICC 102 thereof—between a sinistral side of the RICC insertion assembly 100 and a dextral side of the RICC insertion assembly 100 to accommodate both left-handed and right-handed venipunctures with the RICC insertion assembly 100. Indeed, the swivel arm 182 is configured to flip the loop from the sinistral side of the RICC insertion assembly 100 as shown in FIG. 1 to the dextral side of the RICC insertion assembly 100 to accommodate a left-handed venipuncture with the RICC insertion assembly 100. Likewise, the swivel arm 182 is configured to flip the loop from the dextral side of the RICC insertion assembly 100 to the sinistral side of the RICC insertion assembly 100 to accommodate a right-handed venipuncture with the RICC insertion assembly 100.

Figure 8:
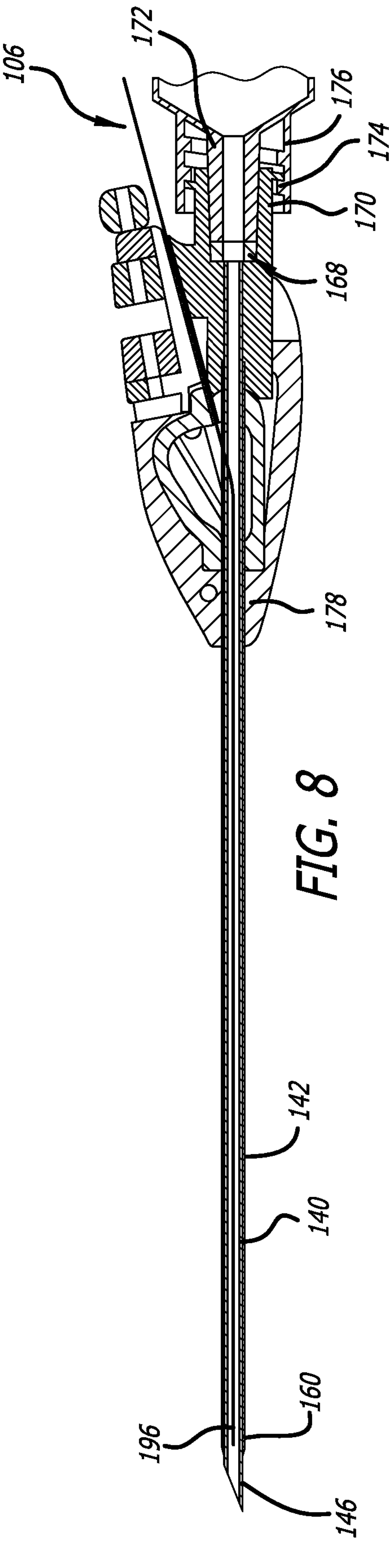
FIG. 8 illustrates a longitudinal cross section of the coupler, the introducer needle, and an access guidewire of the RICC insertion assembly in accordance with some embodiments.
Figure 9:
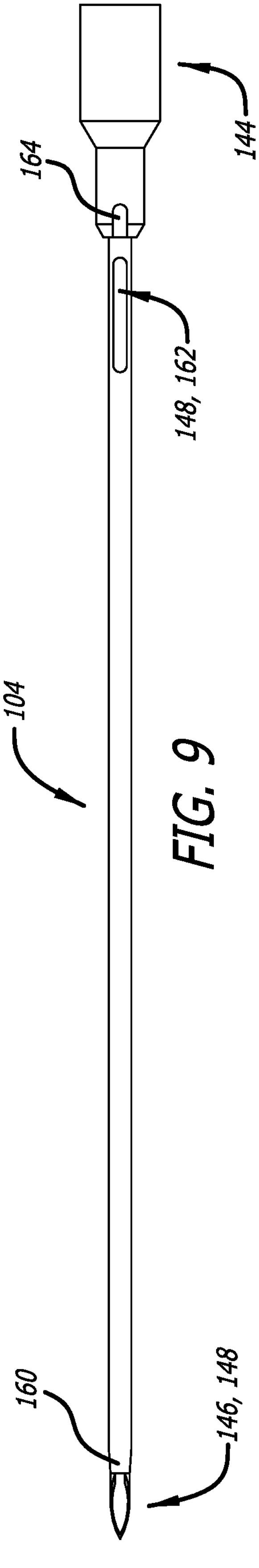
FIG. 9 illustrates a top view of the introducer needle in accordance with some embodiments.
Figure 10:
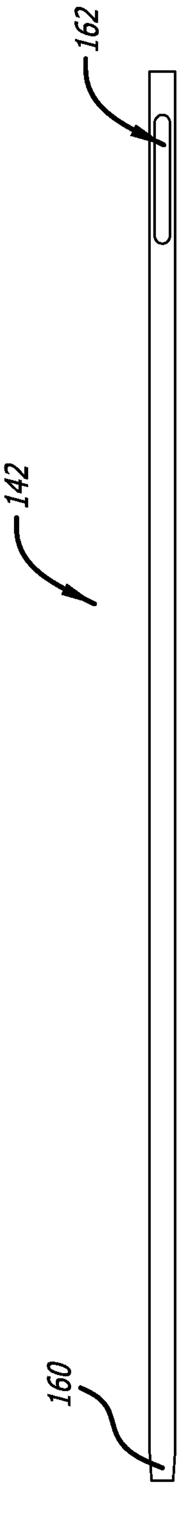
FIG. 10 illustrates a sheath of the introducer needle in accordance with some embodiments.
Figure 11:
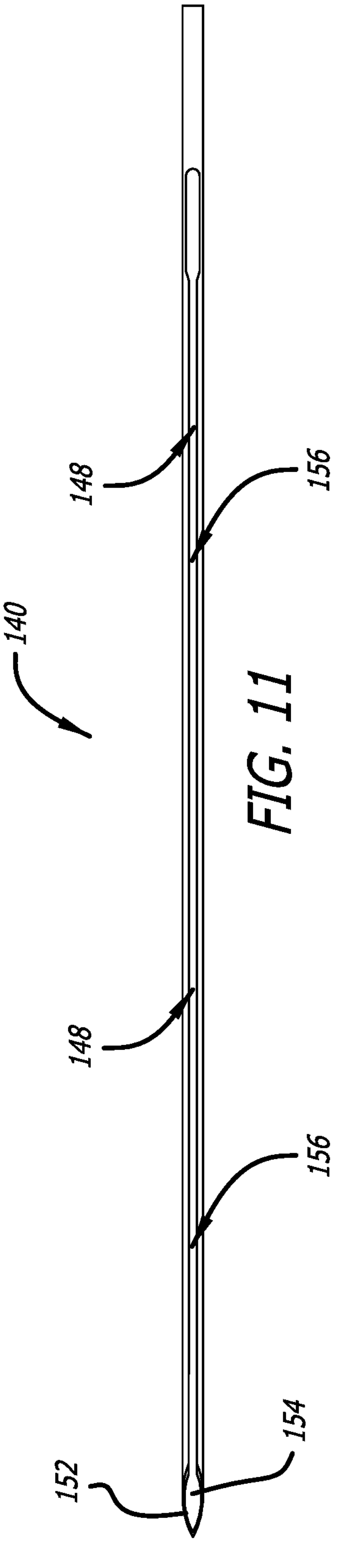
FIG. 11 illustrates a needle shaft of the introducer needle in accordance with some embodiments.

FIGS. 1, 2, and 8 illustrate various view of the access guidewire 106 of the RICC insertion assembly 100 in accordance with some embodiments.

The access guidewire 106 includes a proximal portion including a proximal end and a distal portion including a distal end. In the ready-to-deploy state of the RICC insertion assembly 100, the proximal end of the access guidewire 106 is coupled to the swivel arm 182, particularly the access-guidewire attachment point within the swivel-arm connector 194 of the swivel arm 182. In addition, the proximal portion of the access guidewire 106 extends along the primary lumen 128 of the RICC 102. The distal portion of the access guidewire 106 also extends along the primary lumen 128 of the RICC 102, but the distal portion of the access guidewire 106 further extends out the distal end of the RICC 102, into the valve module 180 over the needle hub 144 by way of the access-guidewire channel 164, into the needle shaft 140 through both the sheath opening 162 of the sheath 142 and the needle slot 148 of the needle shaft 140, and along the needle lumen 158 of the introducer needle 104 in the ready-to-deploy state of the RICC insertion assembly 100. As shown in FIG. 8, the distal end of the access guidewire 106 is disposed in the needle lumen 158 just proximal of the needle tip 146 in the ready-to-deploy state of the RICC insertion assembly 100. Again, the proximal and distal ends of the access guidewire 106 enforce the loop in the access guidewire 106 in the ready-to-deploy state of the RICC insertion assembly 100, which loop the RICC 102 is disposed over, thereby keeping the RICC insertion assembly 100 in a relatively compact form.

The access guidewire 106 can include a guidewire tip 196 in the distal portion of the access guidewire 106, which adopts a T shape configured to prevent puncturing a back wall of a blood vessel. Such a guidewire tip assumes a straightened state in the ready-to-deploy state of the RICC insertion assembly 100 and a curved state when the guidewire tip 196 is advanced beyond the needle tip 146 (e.g., advanced into a blood-vessel lumen) in a deployed state of the RICC insertion assembly 100.

The access guidewire 106 can further include a bare-wire portion and a wound-wire portion distal of the bare-wire portion, proximal of the bare-wire portion, or both. While not shown, the bare-wire portion, when present, distally extends through the access-guidewire conduit 190 of the valve module 180 in at least the ready-to-deploy state of the RICC insertion assembly 100 such that the valve module 180 forms a fluid-tight seal around the bare-wire portion of the access guidewire 106. Notably, the foregoing bare-wire portion can instead be a flat-wound or ground-wound portion of the access guidewire 106, wherein the flat-wound portion includes windings of a tape instead of a round wire, and wherein the ground-wound portion includes windings of a round wire ground down to flatten the windings.

Methods

FIGS. 17-21 illustrate various steps a method of using the RICC insertion assembly 100 in accordance with some embodiments.

As shown, methods of the RICC insertion assembly 100 include a method for inserting the RICC 102 into a blood-vessel lumen of a patient. Such a method includes one or more steps selected from an insertion assembly-obtaining step, a needle tract-establishing step, a blood-aspirating step, an access guidewire-advancing step, an introducer needle-withdrawing step, a RICC-advancing step, an access guidewire-withdrawing step, a maneuver guidewire-advancing step, another RICC-advancing step, and a maneuver guidewire-withdrawing step.

The insertion assembly-obtaining step includes obtaining the RICC insertion assembly 100. A set forth above, the RICC insertion assembly 100 includes the RICC 102, the introducer needle 104 including the sheath 142 over the needle shaft 140, and the access guidewire 106 coupled together by the coupler 108. The proximal end of the access guidewire 106 is coupled to the swivel arm 182 of the coupler 108 while the distal end of the access guidewire 106 is disposed in the introducer needle 104 by way of the valve module 180 of the coupler 108. Again, the proximal and distal ends of the access guidewire 106 enforce a loop in the access guidewire 106 as a result. The RICC 102 is disposed over the loop of the access guidewire 106 in the ready-to-deploy state of the RICC insertion assembly 100.

Figure 17:
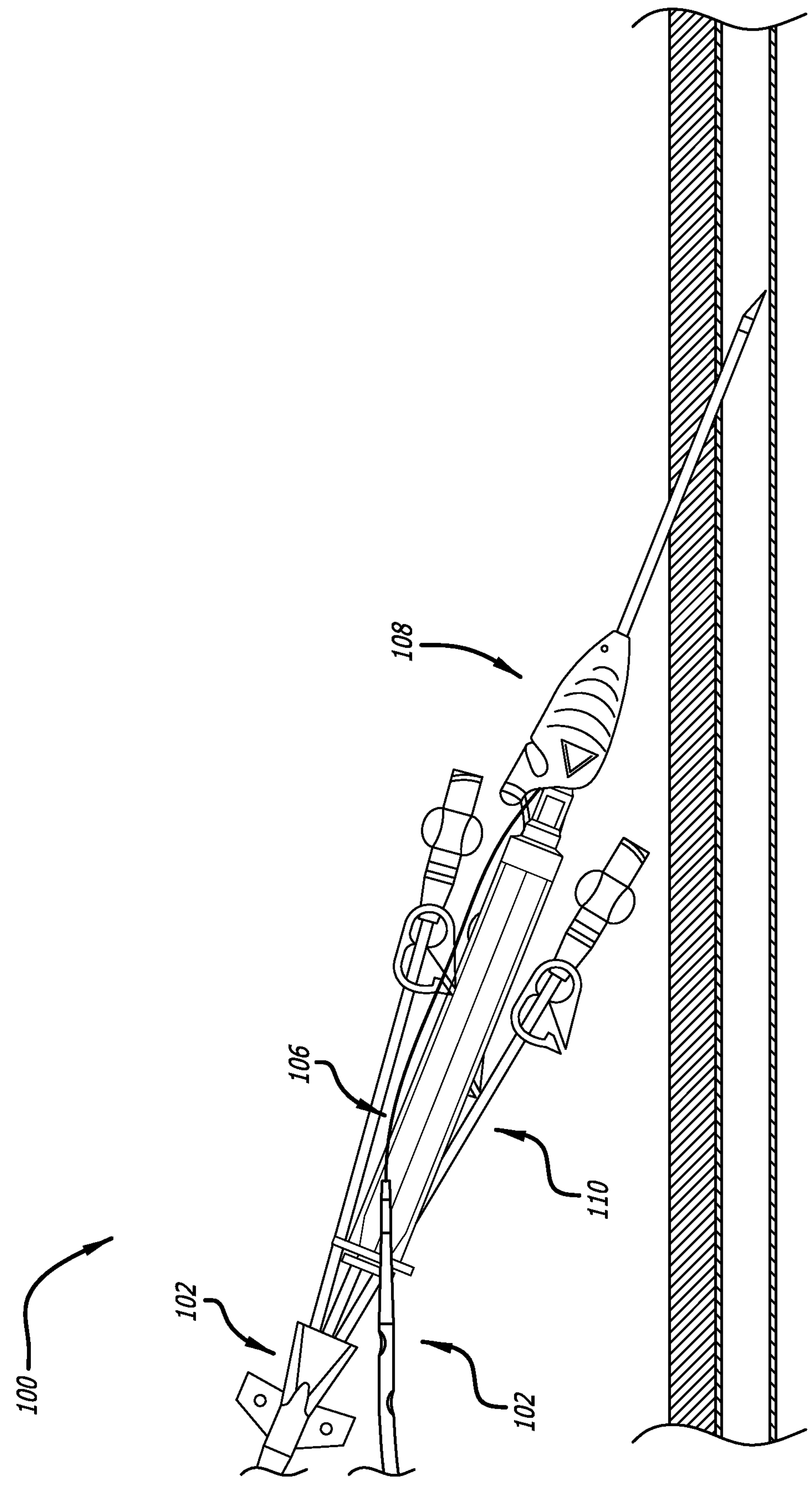
FIG. 17 illustrates a needle tract-establishing step of a method of using the RICC insertion assembly in accordance with some embodiments.

FIG. 17 illustrates a needle tract-establishing step of the method in accordance with some embodiments.

The needle tract-establishing step includes establishing a needle tract from an area of skin to the blood-vessel lumen with the introducer needle 104. Such a needle tract-establishing step can include flipping the swivel arm 182, and, thus, the loop between two sides of the RICC insertion assembly 100 before puncturing the area of skin with the introducer needle 104. The needle tract-establishing step can also include ensuring blood flashback while establishing the needle tract.

Flipping the swivel arm 182 and, thus, the loop between the two sides of the RICC insertion assembly 100 include flipping the loop between a sinistral side of the RICC insertion assembly 100 for a left-handed venipuncture and a dextral side of the RICC insertion assembly 100 for a right-handed venipuncture with the RICC insertion assembly 100. Indeed, flipping the loop from the sinistral side of the RICC insertion assembly 100 to the dextral side of the RICC insertion assembly 100 accommodates a left-handed venipuncture with the RICC insertion assembly 100. Likewise, flipping the loop from the dextral side of the RICC insertion assembly 100 to the sinistral side of the RICC insertion assembly 100 accommodates a right-handed venipuncture with the RICC insertion assembly 100.

Ensuring blood flashback while establishing the needle tract includes ensuring blood flashes back into the needle hub 144 of the introducer needle 104, the syringe tip 172 of the syringe 110 fluidly connected to the introducer needle 104, a barrel of the syringe 110, or a combination thereof. A slight vacuum can be drawn with the syringe 110 while establishing the needle tract such that the blood flashes back into at least the needle hub 144 of the introducer needle 104 upon establishing the needle tract. Ensuring the blood flashes back in accordance with the foregoing confirms the needle tract extends into the blood-vessel lumen.

Figure 18:
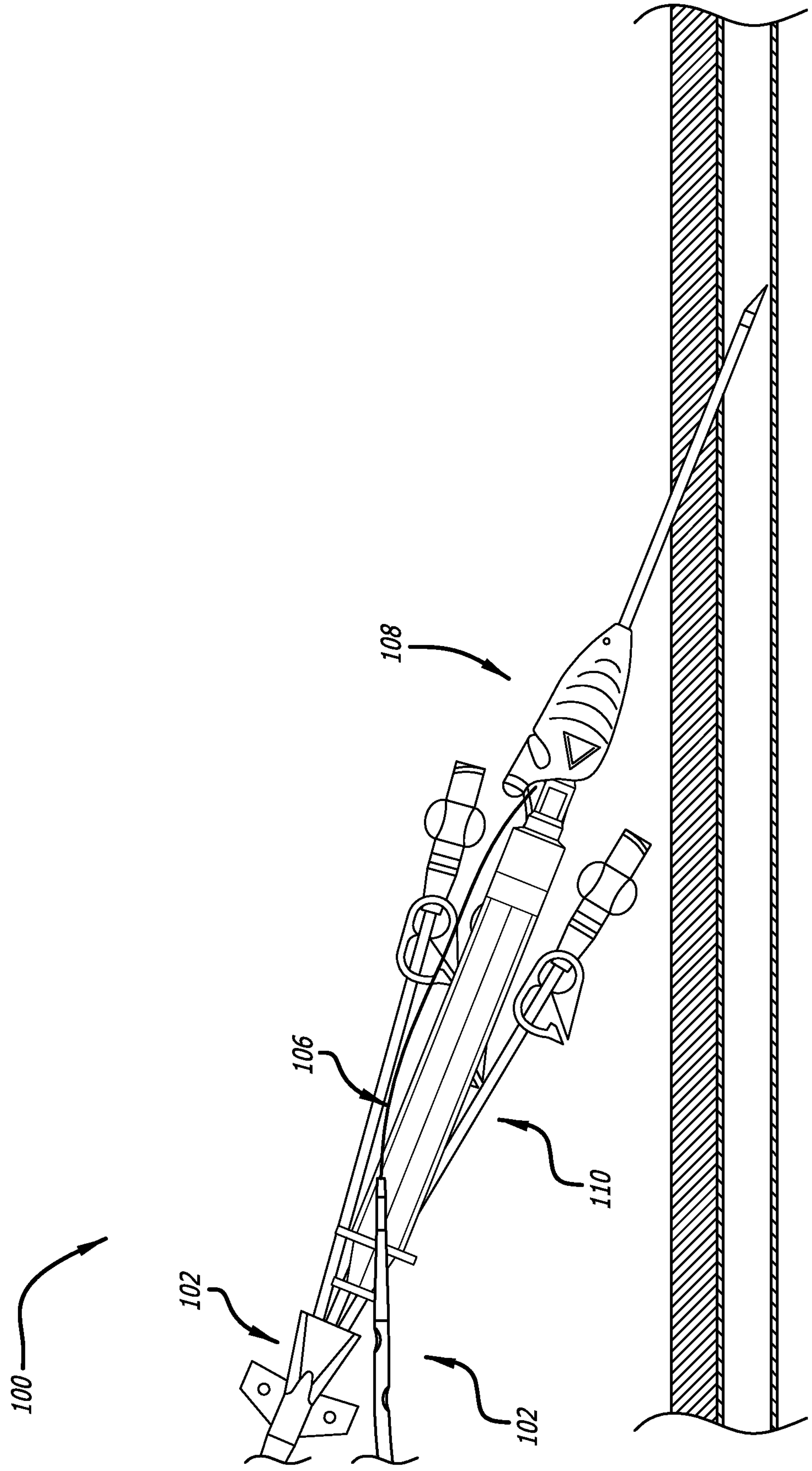
FIG. 18 illustrates a blood-aspirating step of the method in accordance with some embodiments.

FIG. 18 illustrates a blood-aspirating step of the method in accordance with some embodiments.

The blood-aspirating step includes aspirating blood with the syringe 110 for confirmation the needle tract extends into the blood-vessel lumen before withdrawing the introducer needle 104 from the coupler 108 in the introducer needle-withdrawing step. Again, the sheath 142 over the needle shaft 140 seals the needle slot 148 of the needle shaft 140 thereunder. In particular, the sheath 142 seals the needle slot 148 outside of the valve module 180. The valve module 180, in turn, seals over the sheath opening 162 of the sheath 142, which sheath opening 162 allows the access guidewire 106 to pass into the needle shaft 140 by way of the needle slot 148 in the ready-to-deploy state of the RICC insertion assembly 100. The valve module 180 also seals around the distal portion of the access guidewire 106. Such seals enable the syringe 110 to aspirate blood in the blood-aspirating step.

Figure 19:
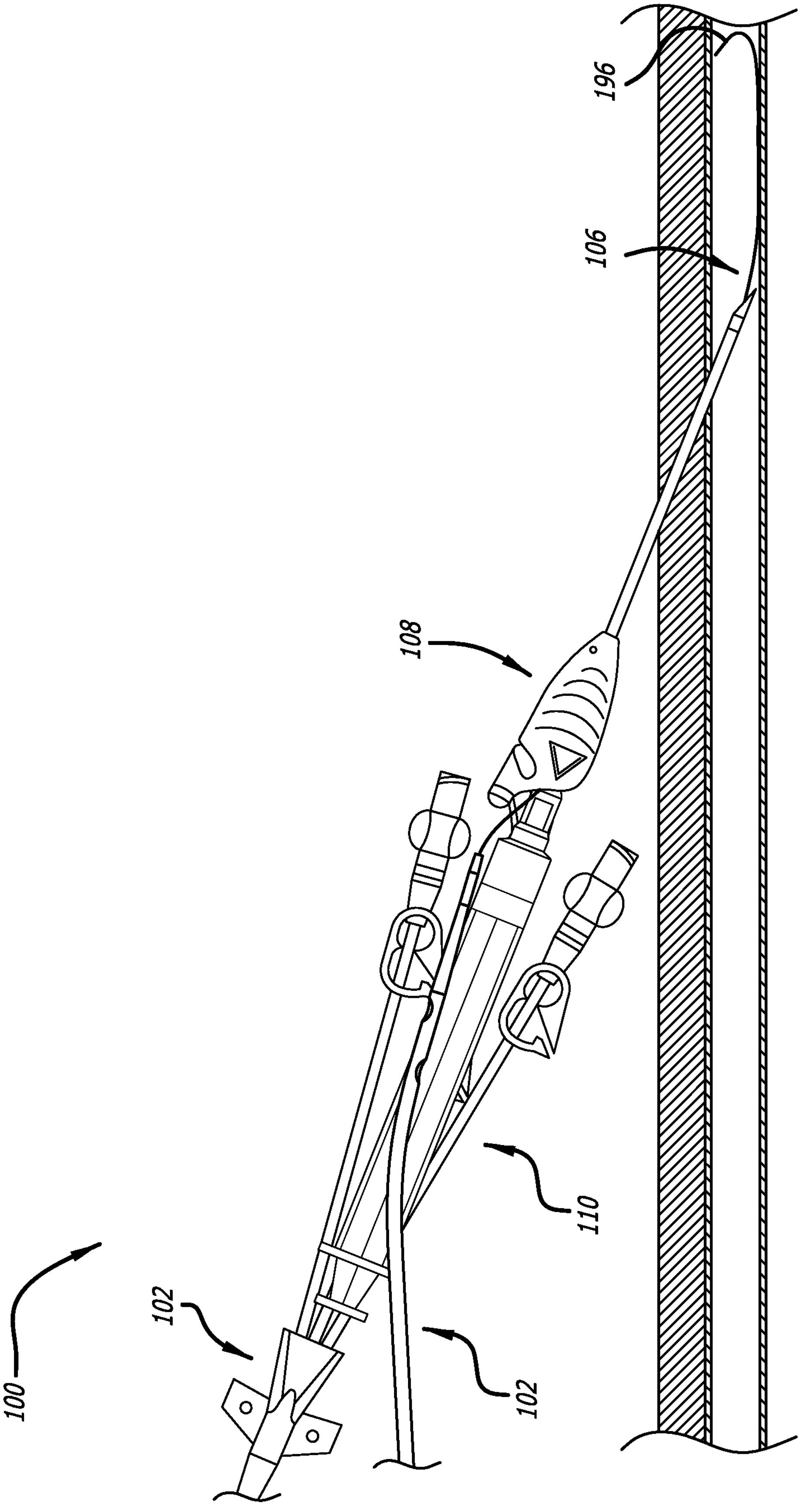
FIG. 19 illustrates an access guidewire-advancing step of the method in accordance with some embodiments.

FIG. 19 illustrates an access guidewire-advancing step of the method in accordance with some embodiments.

The access guidewire-advancing step includes advancing the distal end of the access guidewire 106 from its initial location in the needle shaft 140 just proximal of the needle tip 146 into the blood-vessel lumen, thereby securing blood-vessel access for the RICC 102 in the RICC-advancing step.

Figure 20:
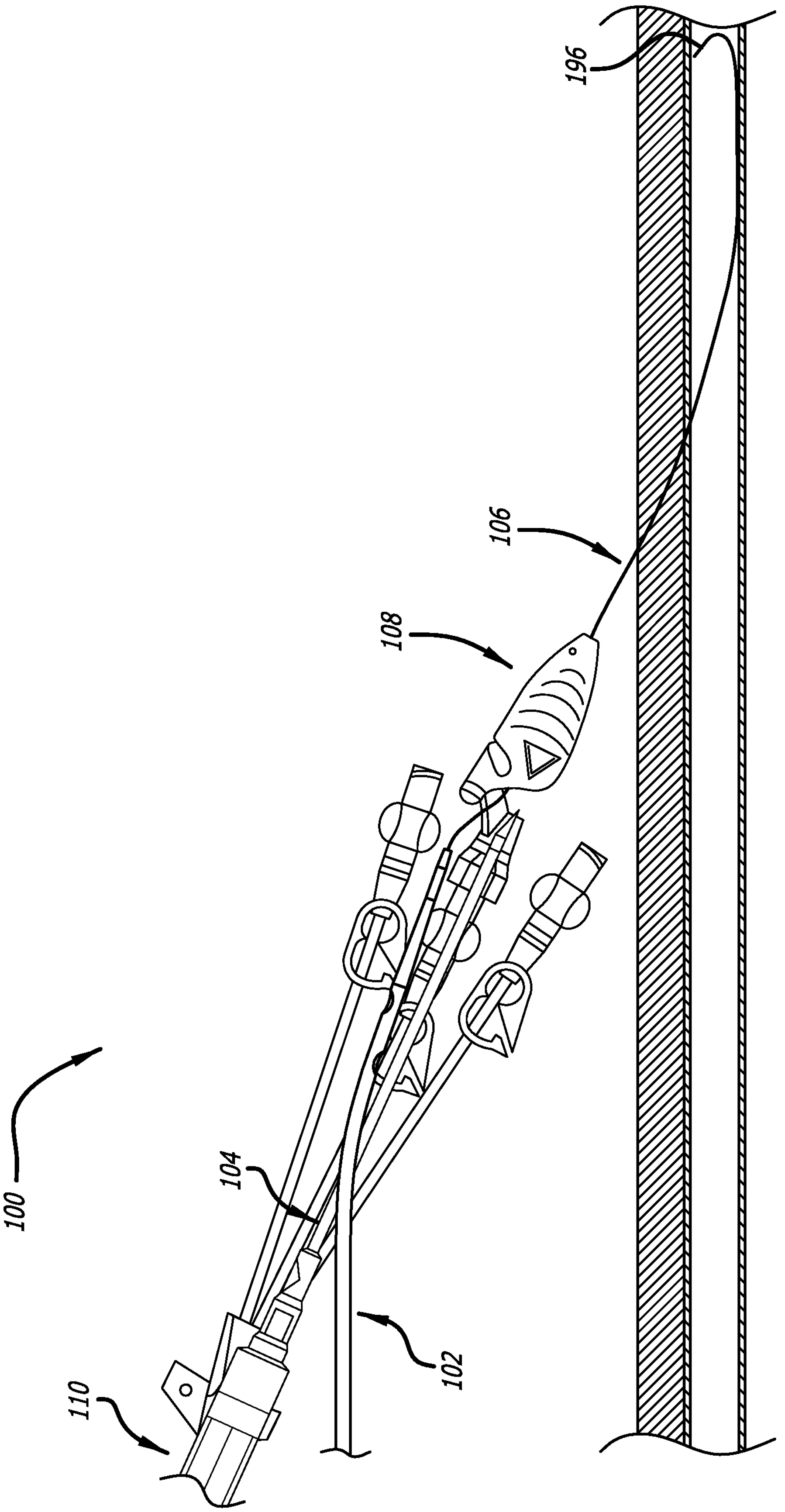
FIG. 20 illustrates an introducer needle-withdrawing step of the method in accordance with some embodiments.

FIG. 20 illustrates an introducer needle-withdrawing step of the method in accordance with some embodiments.

The introducer needle-withdrawing step includes withdrawing the introducer needle 104 from the coupler 108 leaving the access guidewire 106 in place in the blood-vessel lumen. The introducer needle-withdrawing step includes simultaneously cutting the sheath 142 off the needle shaft 140 with the blade 192 of the valve module 180 when the introducer needle 104 is withdrawn from the coupler 108. The cutting of the sheath 142 off the needle shaft 140 allows the access guidewire 106 to escape from the needle shaft 140 by way of the needle slot 148 thereof. Again, the introducer needle 104 includes the needle slot 148 extending from the proximal portion of the needle shaft 140 through the needle tip 146, which allows the access guidewire 106 to escape from the introducer needle 104 with the cutting of the sheath 142 off the needle shaft 140. Notably, the separable pieces of the valve module 180 around the needle shaft 140 and the sheath 142 in the ready-to-deploy state of the RICC insertion assembly 100 separate to allow the access guidewire 106 to further escape from the valve module 180 when the introducer needle 104 is withdrawn from the coupler 108 in the introducer needle-withdrawing step. In addition, the coupler housing 178 includes the coupler-housing slot 186 configured to allow the access guidewire 106 to yet further escape from the coupler housing 178 when the introducer needle 104 is withdrawn from the coupler 108 in the introducer needle-withdrawing step. (See, for example, FIG. 21, wherein the distal portion of the access guidewire 106 has completely escaped from the coupler 108 and the proximal end of the access guidewire 106 remains attached to the access-guidewire attachment point within the swivel-arm connector 194.)

Figure 21:
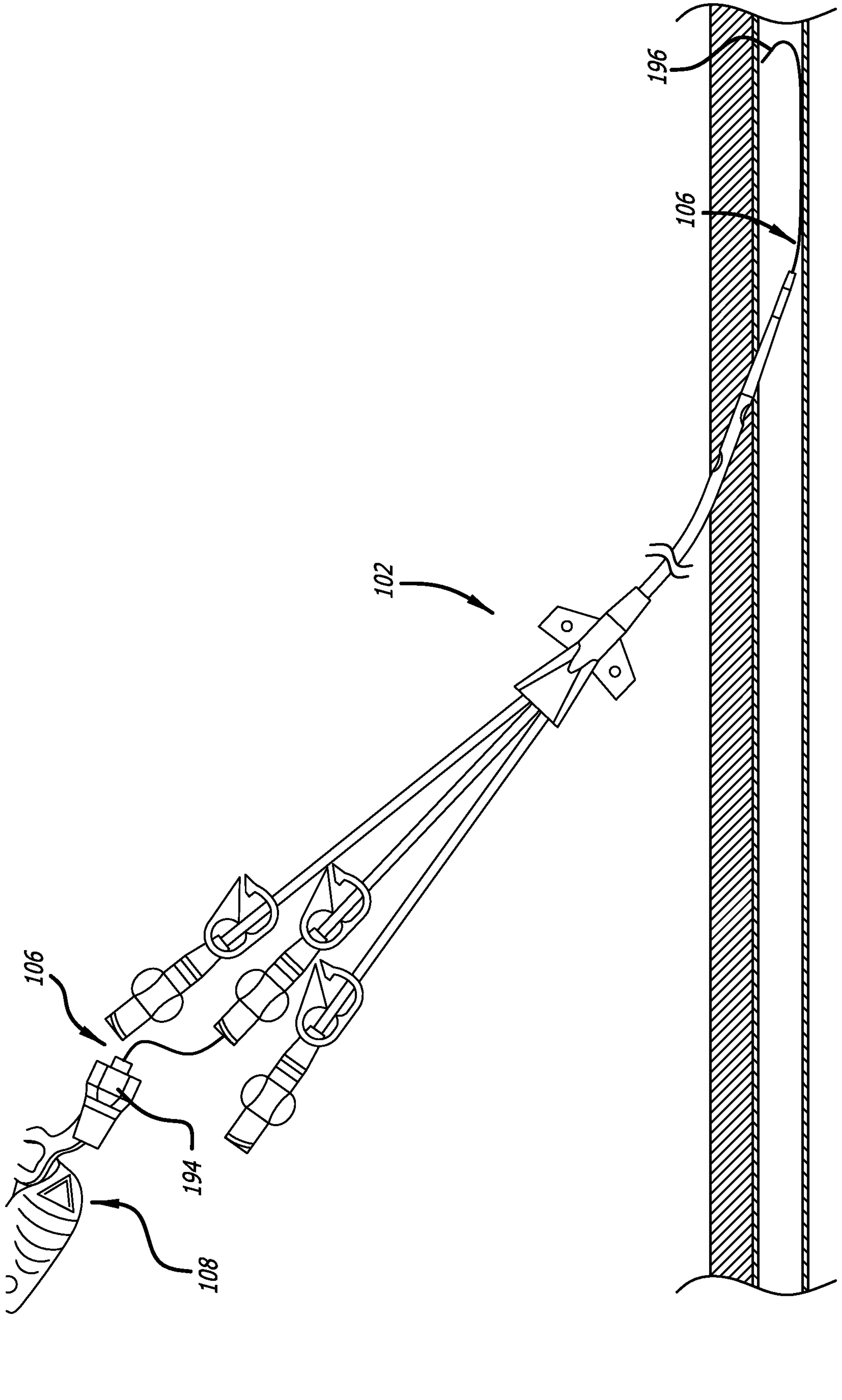
FIG. 21 illustrates a RICC-advancing step of the method in accordance with some embodiments.

FIG. 21 illustrates a RICC-advancing step of the method in accordance with some embodiments.

The RICC-advancing step includes advancing the catheter tube 112 of the RICC 102 over the access guidewire 106 and into the blood-vessel lumen, thereby inserting the RICC 102 into the blood-vessel lumen.

The access guidewire-withdrawing step includes withdrawing the access guidewire 106 leaving the catheter tube 112 in place in the blood-vessel lumen.

The maneuver guidewire-advancing step includes advancing a maneuver guidewire into the blood-vessel lumen by way of the primary lumen 128 of the RICC 102 and to a lower ⅓ of an SVC of a heart of the patient.

The other RICC-advancing step includes advancing the distal portion of the catheter tube 112 farther into the blood-vessel lumen over the maneuver guidewire to the lower ⅓ of the SVC of the heart of the patient.

The maneuver guidewire-withdrawing step includes withdrawing the maneuver guidewire leaving the catheter tube 112 in place in the lower ⅓ of the SVC.

While some particular embodiments have been disclosed herein, and while the particular embodiments have been disclosed in some detail, it is not the intention for the particular embodiments to limit the scope of the concepts provided herein. Additional adaptations or modifications can appear to those of ordinary skill in the art, and, in broader aspects, these adaptations or modifications are encompassed as well. Accordingly, departures may be made from the particular embodiments disclosed herein without departing from the scope of the concepts provided herein.

What is claimed is:

1. A rapidly insertable central catheter ("RICC") insertion assembly, comprising:

- a RICC including:
  - a catheter tube;
  - a catheter hub coupled to a proximal portion of the catheter tube;
  - one or more extension legs, each extension leg of the one or more extension legs coupled to the catheter hub by a distal portion thereof; and
  - one or more extension-leg connectors, each extension-leg connector of the one or more extension-leg connectors disposed over a proximal portion of an extension leg of the one or more extension legs;
- an introducer needle including:
  - a needle shaft including a longitudinal needle slot extending from a proximal portion of the needle shaft through a needle tip in a distal portion of the needle shaft;
  - a sheath over the needle shaft, the sheath including a sheath opening in a proximal portion of the sheath; and
  - a needle hub over the proximal portion of the needle shaft and the proximal portion of the sheath;
- a coupler coupling the RICC and the introducer needle together in a ready-to-deploy state of the RICC insertion assembly, the coupler including:
  - a coupler housing including a needle-hub receptacle, the needle hub inserted into the needle-hub receptacle;
  - a valve module disposed in the coupler housing, the needle shaft and the sheath extending from the needle hub, through the valve module, and out a distal end of the coupler housing; and
  - a swivel arm swivelably coupled to the coupler housing, the swivel arm including a swivel-arm connector connected to an extension-leg connector of the one or more extension-leg connectors; and
- an access guidewire including:
  - a proximal end coupled to the swivel-arm connector;
  - a proximal portion extending along a primary lumen of the RICC;
  - a distal portion extending along the primary lumen of the RICC, out a distal end of the RICC, into the valve module over the needle hub, into the needle shaft through both the sheath opening and the longitudinal needle slot, and along a needle lumen of the introducer needle; and
  - a distal end disposed in the needle lumen just proximal of the needle tip.

2. The RICC insertion assembly of claim 1, further comprising a syringe fluidly coupled to the introducer needle in the ready-to-deploy state of the RICC insertion assembly, the sheath sealing the longitudinal needle slot of the needle shaft thereunder outside of the valve module, the valve module sealing the sheath opening of the sheath therein, and the valve module sealing around the access guidewire enabling the syringe to aspirate blood.

3. The RICC insertion assembly of claim 1, wherein the proximal end of the access guidewire coupled to the swivel-arm connector and the distal end of the access guidewire disposed in the needle lumen enforces a loop in the access guidewire over which the RICC is disposed in the ready-to-deploy state of the RICC insertion assembly.

4. The RICC insertion assembly of claim 3, wherein the swivel arm is configured to flip the loop between a sinistral side of the RICC insertion assembly and a dextral side of the RICC insertion assembly to accommodate both left-handed and right-handed venipunctures with the RICC insertion assembly.

5. The RICC insertion assembly of claim 1, wherein the coupler includes a needle-hub lock configured to lock the needle hub in the needle-hub receptacle, a pair of lock buttons of the needle-hub lock distributed between opposing sides of the coupler configured to unlock the needle hub when the lock buttons are pressed into the coupler for withdrawal of the introducer needle from the coupler.

6. The RICC insertion assembly of claim 1, wherein the valve module includes an integrated blade disposed in the longitudinal needle slot under a distal end of the sheath opening, the integrated blade including a distal facing blade edge configured to cut the sheath off the needle shaft as the introducer needle is withdrawn from the coupler, thereby allowing the access guidewire to escape from the needle shaft by way of the longitudinal needle slot thereof.

7. The RICC insertion assembly of claim 1, wherein the coupler housing includes a longitudinal coupler-housing slot configured to allow the access guidewire to escape from the coupler housing when the introducer needle is withdrawn from the coupler.

8. The RICC insertion assembly of claim 1, wherein the valve module includes separable pieces around the needle shaft and the sheath configured to separate and allow the access guidewire to escape from the valve module when the introducer needle is withdrawn from the coupler.

9. The RICC insertion assembly of claim 1, the catheter tube including:

a first section formed of a first polymeric material having a first durometer, the first section in a distal portion of the catheter tube;

a second section formed of a second polymeric material having a second durometer less than the first durometer, the second section in the distal portion of the catheter tube proximal of the first section of the catheter tube; and a tapered junction between the first section and the second section of the catheter tube, the tapered junction having a length between that of exposed portions of the first section and the second section of the catheter tube.

10. The RICC insertion assembly of claim 9, wherein a proximal portion of the first section of the catheter tube is disposed in a bore in a distal portion of the tapered junction and bonded thereto.

11. The RICC insertion assembly of claim 9, wherein a distal end of the second section of the catheter tube is flush with a proximal end of the tapered junction and bonded thereto.

12. The RICC insertion assembly of claim 9, wherein the catheter tube possess a column strength sufficient to prevent buckling of the catheter tube when inserted into a needle tract established by a percutaneous puncture with the introducer needle and advanced through a vasculature of a patient without dilation of tissue about the needle tract or any blood vessels of the vasculature beforehand with a separate dilator.

13. The RICC insertion assembly of claim 9, wherein the RICC includes a set of three lumens including the primary lumen, a secondary lumen, and a tertiary lumen formed of fluidly connected portions of three catheter-tube lumens, three catheter-hub lumens, and three extension-leg lumens.

14. The RICC insertion assembly of claim 13, wherein the primary lumen has a primary-lumen aperture in a distal end of the catheter tube, the secondary lumen has a secondary-lumen aperture in a side of the distal portion of the catheter tube, and the tertiary lumen has a tertiary-lumen aperture in the side of the distal portion of the catheter tube proximal of the secondary-lumen aperture.

* * * * *